(12) United States Patent
Wittwer et al.

(10) Patent No.: US 7,238,321 B2
(45) Date of Patent: Jul. 3, 2007

(54) METHOD FOR RAPID THERMAL CYCLING OF BIOLOGICAL SAMPLES

(75) Inventors: Carl T. Wittwer, Salt Lake City, UT (US); David R. Hillyard, Salt Lake City, UT (US)

(73) Assignee: University of Utah Research Foundation, Salt Lake City, UT (US)

( * ) Notice: Subject to any disclaimer, the term of this patent is extended or adjusted under 35 U.S.C. 154(b) by 55 days.

(21) Appl. No.: 10/891,161

(22) Filed: Jul. 13, 2004

(65) Prior Publication Data

US 2004/0265892 A1 Dec. 30, 2004

Related U.S. Application Data

(63) Continuation of application No. 09/132,156, filed on Aug. 11, 1998, now Pat. No. 6,787,338, which is a continuation of application No. 08/537,612, filed on Oct. 2, 1995, now abandoned, which is a continuation-in-part of application No. 08/179,969, filed on Jan. 10, 1994, now Pat. No. 5,455,175, which is a continuation-in-part of application No. 07/815,966, filed on Jan. 2, 1993, now abandoned, which is a continuation-in-part of application No. 07/534,029, filed on Jun. 4, 1990, now abandoned.

(51) Int. Cl.
*G01N 1/00* (2006.01)
*G01N 15/00* (2006.01)
*B10J 19/18* (2006.01)
*C12P 19/34* (2006.01)

(52) U.S. Cl. .................. 422/50; 422/68.1; 422/134; 435/91.2

(58) Field of Classification Search ................ 422/129; 712/206
See application file for complete search history.

(56) References Cited

U.S. PATENT DOCUMENTS 3,616,264 A 10/1971 Ray et al.

(Continued)

FOREIGN PATENT DOCUMENTS

DE 3808942 A1 9/1989

(Continued)

OTHER PUBLICATIONS

Instruction manuel for the Perkin-Elmer Cetus DNA Thermal Cycler, Mar. 1988.*

(Continued)

*Primary Examiner*—Ram R. Shukla
*Assistant Examiner*—Anna Skibinsky
(74) *Attorney, Agent, or Firm*—Morgan Lewis & Bockius LLP; Richard F. Trecartin

(57) ABSTRACT

A thermal cycling method and device is disclosed. The device comprises a sample chamber whose temperature can be rapidly and accurately modulated over a range of temperatures needed to carry out a number of biological procedures, such a DNA polymerase chain reaction. Biological samples are placed in glass micro capillary tubes and then located inside the sample chamber. A programmable controller regulates the temperature of the sample inside the sample chamber. Once a heating cycle is completed, the controller opens a door to the chamber for venting hot air out and cool ambient air is moved in. Temperature versus time profiles corresponding to optimum denaturation, annealing and elongation temperatures for amplification of DNA are achieved by the present invention.

13 Claims, 13 Drawing Sheets

U.S. PATENT DOCUMENTS

| | | | |
|---|---|---|---|
| 4,038,055 A | | 7/1977 | Varano et al. |
| 4,072,187 A | * | 2/1978 | Lodge ...................... 165/48.1 |
| 4,286,456 A | | 9/1981 | Sista et al. |
| 4,420,679 A | | 12/1983 | Howe |
| 4,599,169 A | | 7/1986 | Ray |
| 4,683,195 A | | 7/1987 | Mullis et al. |
| 4,683,202 A | | 7/1987 | Mullis et al. |
| 4,701,415 A | | 10/1987 | Dutton et al. |
| 4,865,986 A | | 9/1989 | Coy et al. |
| 4,902,624 A | | 2/1990 | Columbus et al. |
| 4,965,188 A | | 10/1990 | Mullis et al. |
| 4,981,801 A | | 1/1991 | Suzuki et al. |
| 5,038,852 A | * | 8/1991 | Johnson et al. ............. 165/267 |
| 5,139,940 A | * | 8/1992 | Isaacs et al. .................... 435/6 |
| 5,187,084 A | * | 2/1993 | Hallsby ..................... 435/91.2 |

FOREIGN PATENT DOCUMENTS

| | | |
|---|---|---|
| WO | WO 8909437 | 10/1989 |

OTHER PUBLICATIONS

"Minimizing the Time Required for DNA Amplification by Efficient Heat Transfer to Small Samples," Analytical Biochemistry, 186:328-331 (1990).

Cao, "A Simple and Inexpensive System to Amplify DNA by PCR," Biotechniques, 7(6):566-567(1989).

Denton et al., "A Low-Cost Air-Driven Cycling Oven," PCR Protocols: A Guide to Methods and Applications, 435-441 (1990).

Hoffman et al., "Use of a Gas Chromatograph Oven for DNA Amplification by the Polymerase Chain Reaction," Biotechniques, 6(10):932-936 (1988).

Linz, "Thermocycler Temperature Variation Invalidates PCR Results," Biotechniques, 9(3):286-290 (1990).

Wittwer et al., "Automated Polymerase Chain Reaction in Capillary Tubes with Hot Air," Nucleic Acids Research, 17(11):4353-4357 (1989).

Instruction Manual for the Perkin-Elmer Celus DNA Thermal Cycler, Mar. 1988.

Morrison, et al. "Solution-Phase Detection of Polynucleotides Using Interacting Fluorescent Labels and Competitive Hybridization" *Anal Biochem.* 183, pp. 231-244 (1989).

Coy Laboratory Products, Inc. Catalog page for "TempCycler".

Eppendorf Advertisement for "Eppendorf MicroCycler™".

Hybaid Advertisement for "Heating and Cooling Block" *Products & Materials*, Sep. 9, 1988, p. 1371.

Rollo F., et al. "A simple and low cost DNA amplifer" *Nucleic Acids Research* vol. 16, No. 7, (1988), pp. 3105-3106.

Wittwer, et al. Minimizing the Time Required for DNA Amplification by Efficient Heat Transfer to Small Samples: *Anal.Biochem.* (1990) vol. 186, pp. 328-331.

* cited by examiner

Effect of Annealing Time on Product Yield and Background Amplification

Effect of Denaturation Time on Product Yield

METHOD FOR RAPID THERMAL CYCLING OF BIOLOGICAL SAMPLES

RELATED APPLICATIONS

This application is a continuation application of U.S. application Ser. No 09/132,156, filed Aug. 11, 1998 now U.S. Pat. No. 6,787,338, which is a continuation of U.S. patent application Ser. No. 08/537,612 filed Oct. 2, 1995, now abandoned entitled Method for Rapid Thermal Cycling of Biological Samples which is a continuation-in-part of U.S. patent application Ser. No. 08/179,969 filed Jan. 10, 1994 entitled Rapid Thermal Cycling Device, U.S. Pat. No. 5,455,175 issued on Oct. 3, 1995, which is a continuation-in-part of U.S. patent application Ser. No. 07/815,966 filed Jan. 2, 1993 entitled Rapid Thermal Cycling Device, now abandoned, which is a continuation-in-part of U.S. patent application Ser. No. 07/534,029 filed Jun. 4, 1990 entitled Automated Polymerase Chain Reaction Device, now abandoned.

BACKGROUND

1. The Field of the Invention

This invention relates generally to apparatus for rapid control of the temperature of a liquid sample. More specifically, the present invention relates to thermal cycling apparatus for precisely controlling and rapidly varying the temperature of a sample repeatedly through a predetermined temperatures cycle.

2. The Background Art

In numerous areas of industry, technology, and research there is a need to reliably and reproducibly subject relatively small samples to thermal cycling. The need to subject a sample to repeated thermal cycles is particularly acute in biotechnology applications. In the biotechnology field, it is often desirable to repeatedly heat and cool small samples of materials over a short period of time. One such biological process that is regularly carried out is cyclic DNA amplification.

Cyclic DNA amplification, using thermostable DNA polymerase, allows automated amplification of primer specific DNA, widely known as the "polymerase chain reaction." Automation of this process requires controlled and precise thermal cycling of reaction mixtures usually contained in a plurality of containers. In the past, the container of preference has been a standard, plastic microfuge tube.

Commercial programmable metal heat blocks have been used in the past to effect the temperature cycling of samples in microfuge tubes through the desired temperature versus time profile. However, the inability to quickly and accurately adjust the temperature of the heat blocks through a large temperature range over a short time period, has rendered the use of heat block type devices undesirable as a heat control system when carrying out the polymerase chain reaction.

Moreover, the microfuge tubes which are generally used have disadvantages. The material of the microfuge tubes, their wall thickness, and the geometry of microfuge tubes is a hinderance to rapid heating and cooling of the sample contained therein. The plastic material and the thickness of the wall of microfuge tubes act as an insulator between the sample contained therein and the surrounding medium thus hindering transfer of thermal energy. Also, the geometry of the microfuge tube presents a small surface area to whatever medium is being used to transfer thermal energy. The continued use of microfuge tubes in the art, with their suboptimal geometry, indicates the benefits of improved thermal transfer (which come by increasing the surface area of a sample container for a sample of constant volume) has heretofore not been recognized.

Furthermore, devices using water baths with fluidic switching, (or mechanical transfer) have also been used as a thermal cycler for the polymerase chain reaction. Although water baths have been used in cycling a polymerase chain reaction mixture through a desired temperature versus time profile necessary for the reaction to take place, the high thermal mass of the water (and the low thermal conductivity of plastic microfuge tubes), has been significantly limiting as far as performance of the apparatus and the yields of the reactions are concerned.

Devices using water baths are limited in their performance. This is because the water's thermal mass significantly restricts the maximum temperature versus time gradient which can be achieved thereby. Also, the water bath apparatus has been found to be very cumbersome due to the size and number of water carrying hoses and external temperature controlling devices for the water. Further, the need for excessive periodic maintenance and inspection of the water fittings for purposes of detecting leaks in a water bath apparatus is tedious and time consuming. Finally, it is difficult with the water bath apparatus to control the temperature in the sample tubes with the desired accuracy.

U.S. Pat. No. 3,616,264 to Ray shows a thermal forced air apparatus for cycling air to heat or cool biological samples to a constant temperature. Although the Ray device is somewhat effective in maintaining a constant temperature within an air chamber, it does not address the need for rapidly adjusting the temperature in a cyclical manner according to a temperature versus time profile such as is required for biological procedures such as the polymerase chain reaction.

U.S. Pat. No. 4,420,679 to Howe and U.S. Pat. No. 4,286,456 to Sisti et al. both disclose gas chromatograhic ovens. The devices disclosed in the Howe and Sisti et al. patents are suited for carrying out gas chromatography procedures but do not provide thermal cycling which is substantially any more rapid than that provided by any of the earlier described devices. Rapid thermal cycling, while potentially useful for many procedures, is particularly advantageous for carrying out the polymerase chain reaction. Devices such as those described in the Howe and Sisti et al. patents are not suitable for efficiently and rapidly carrying out such reactions.

BRIEF SUMMARY AND OBJECTS OF THE INVENTION

In view of the above described state of the art, the present invention seeks to realize the following objects and advantages.

It is an object of the present invention to provide an apparatus for accurately controlling the temperature of biological samples.

It is a further object of the present invention to provide thermal cycling apparatus for quickly and accurately varying the temperature of biological samples according to a predetermined temperature versus time profile.

It is another object of the present invention to provide an apparatus suitable for subjecting a number of different biological samples to rapid thermal cycling.

It is also an object of the present invention to provide a thermal cycling apparatus having a thermal transfer medium of low thermal mass which can effectively subject samples to a large temperature gradient over a very short period of time.

It is a further object of the present invention to provide an apparatus which can subject a biological sample to rapid thermal cycling using air as a thermal transfer medium.

It is another object of the present invention to provide a thermal cycling apparatus which will heat samples located in a fluid chamber therein, by means of an internal heater, and will subsequently cool the samples by moving ambient fluid into the chamber, at the proper time in the thermal cycle, to cool the samples.

These and other objects and advantages of the invention will become more fully apparent from the description and claims which follow, or may be learned by the practice of the invention.

The present invention is an apparatus particularly suited for subjecting biological samples to rapid thermal cycling in order to carry out one or more of a number of procedures or processes. In one of its preferred forms, the apparatus includes a means for holding a biological sample. The means for holding a biological sample, or a sample chamber, is provided with an insulation means for retaining thermal energy and also a means for heating the interior of the sample chamber. Preferably, a high wattage incandescent lamp functions as a means for heating the interior of the sample chamber. A thermal insulator lines the interior of the sample chamber and functions to retain the heat generated by the lamp within the sample chamber and serves as an insulation means.

In order to rapidly cool the sample chamber, the preferred apparatus includes a means for forcing air into the sample chamber and a means for dispersing the air forced into the sample chamber. A high velocity fan functions to force air into the sample chamber and a rotating paddle functions to disperse the air into the chamber. A means for venting allows the air to escape from the sample chamber taking the unwanted heat with it. The present invention allows heating and cooling of a sample to take place both quickly and uniformly.

The apparatus of the present invention includes a control means for operating the apparatus thought the desired time versus temperature profile. The present invention is particularly well suited for carrying out automated polymerase chain reactions.

Other embodiments of the present invention include a closed loop hot fluid compartment and a reaction compartment. The reaction compartment is located within the hot fluid compartment and can be accessed through a venting door for allowing the insertion of samples in capillary tubes which may contain a reaction mixture for the polymerase chain reaction. A heating coil is also located in the compartment and is regulated by a programmable set-point process controller via a thermocouple sensor which is also located in the compartment at a position directly adjacent to the reaction compartment.

The heat coil is located up-stream of the reaction compartment, and a fan is located up-stream of the heat coil, such that, fluid blown across the heat coil by the blower unit passes through the reaction compartment and into the intake side of the blower unit in closed loop fashion. Baffles may be located between the heat coil and the reaction compartment in order to cause uniform homogenous mixing of the heated fluid before it passes through the reaction compartment.

Alternately, the fan may be placed downstream of the heating coil but before the reaction compartment. In this case, the fan blades serve as baffles to mix the heated fluid. At the correct time in the predetermined thermal cycle, the controller activates a solenoid that opens the venting door which vents fluid out of the compartment and allows cool (ambient) fluid to enter and cool the samples.

The controller of the present invention allows the chamber, and subsequently the samples located in the sample compartment therein, to pass through a predetermined temperature cycle corresponding to the denaturation, annealing and elongation steps in the polymerase chain reaction. In use, the apparatus of the present invention allows rapid optimization of denaturation, annealing, and elongation steps in terms of time and temperature, and shortened time periods (ramp times) between the temperatures at each step.

The present invention particularly decreases the total time required for completion of polymerase chain reaction cycling over prior art thermal cycling devices while at the same time significantly increasing specificity and yield.

BRIEF DESCRIPTION OF THE DRAWINGS

In order to better appreciate how the above-recited and other advantages and objects of the invention are obtained, a more particular description of the invention briefly described above will be rendered by reference to specific embodiments thereof which are illustrated in the appended drawings. Understanding that these drawings depict only a typical embodiment of the invention and are not therefore to be considered limiting of its scope, the invention will be described and explained with additional specificity and detail through the use of the accompanying drawings in which.

DETAILED DESCRIPTION OF THE PREFERRED EMBODIMENTS

Reference will now be made to the drawings wherein like structures will be provide with like reference designations.

Figure 1:
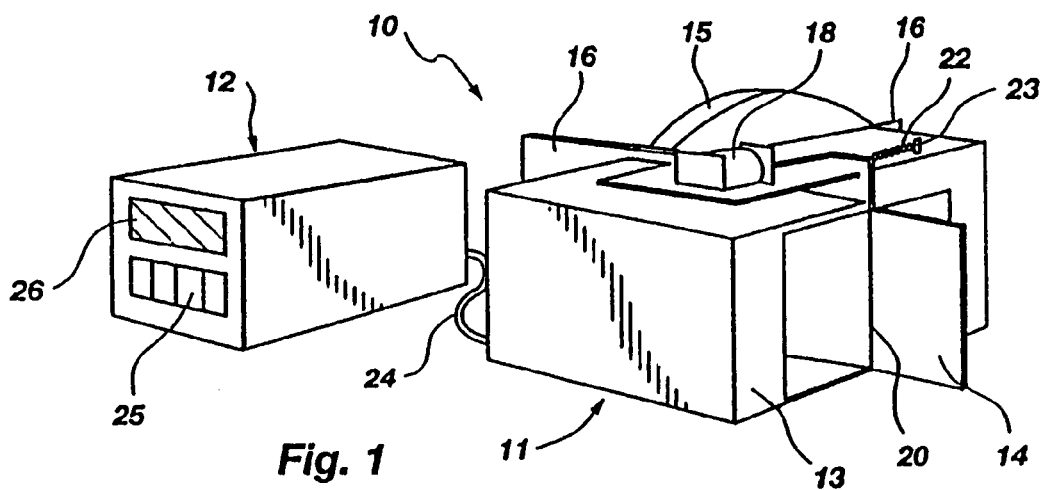
FIG. 1 shows a perspective view of a thermal cycling apparatus adapted for thermal cycling of biological samples and adapted especially for use in cyclic DNA amplification, according to the concepts of the present invention.

As shown in FIG. 1, the thermal cycling device 10 includes a closed loop fluid (most preferably air) chamber, generally designated at 11, which is adapted to accept samples to be cycled through vent door 14. The closed loop fluid chamber 11 includes a plurality of compartments each of which will be described shortly. The device 10 also includes a controller 12 which can be programmed by means of input keys 25 and display 26 to causes the chamber 11 to be cycled through a series of temperatures over a predetermined period of time. The thermal cycling of chamber 11 can be used to carry out numerous procedures and is particularly suited or amplification of primer specific DNA from samples containing reaction mixtures as will be explained below.

The closed loop fluid chamber 11 is enclosed in a generally box shaped configuration by housing 13. Blower mounting boards 16, if desired, can be located so as to section off a smaller rectangular section of the chamber 11 and function to support and secure a generally cylindrically shaped lower housing 15 thereto. Alternatively, the fan of the blower 28 may be housed integrally within chamber housing 13.

The interior of blower housing 15 contains the blades and shaft of the blower. The blower motor (not shown) is located externally of blower housing 15, and therefore exteriorly of the enclosed chamber 11. In this configuration, the blades and shaft are the only parts of the blower which become exposed to the circulating hot fluid within chamber 11. It would be disadvantageous to mount the motor within the chamber which would subject the motor to temperature variations and also would add the thermal mass of the motor to that which is subject to heating and cooling. The reduction of thermal mass exposed to the fluid in chamber 11 is important to the overall performance of the device 10 in its function of subjecting samples placed therein to predetermined temperature versus time profiles as will be more fully explained below.

The blower 28 is a well known type blower usually identified as an "in line" type blower which preferably employs a propeller type fan due to its generally low thermal mass, or if desired, a squirrel cage type fan, the fan preferably having a 75 cubic feed per minute minimum capacity.

The solenoid platform 17 has secured thereto a solenoid 18. the solenoid armature 19 is attached to upper end 21 of rod 20 which is rigidly attached to vent door 14 and rotatably attached to housing 13 at points above and below the vent door 14. The rod 20 therefore allows vent door 14 to freely rotate relative to the housing 13 about the rod's longitudinal axis.

A spring 22 is attached at one of its ends to the housing 13 by support post 23. The opposite end of spring 22 is attached to the top end 21 of rod 20 directly adjacent the attachment of solenoid armature 19. The spring 22 is drawn between these two attachment points so as to be in tension. The spring 22 therefore tends to draw top end 21 toward the support post 23, which in turn tends to rotate vent door 14 to its closed position. When solenoid 18 is actuated, armature 19 tends to pull top end 21 of the rod 20 in the direction of the solenoid 18, which is opposite the direction of pull of spring 22, and which tends to open the vent door 14.

Controller, generally designated at 12, is electrically attached to the chamber 11 by means of a transmission cable 24. The cable 24 also supplies power to the blower motor (not shown), and to the heat coil 31. Further, the controller 12 also is connected to thermocouple sensor 35 for receiving signals corresponding to temperature data, and to solenoid 18 for triggering the solenoid armature.

Controller 12 can be any well known type of temperature controller unit which is programmable to control the heat coil 31, vent door 14, and blower so as to achieve predetermined temperatures as a function of time within the chamber 11, and which is also capable of being programmed to actuate a relay output for driving a solenoid at predetermined time periods and chamber temperature levels. A preferred temperature controller 12 for use in the embodiment of FIGS. 1-3 is a Partlow MIC-6000 proportional temperature controller, available through Omega Engineering Inc, of Stanford Connecticut, as the Model No. CN8600 process controller.

Figure 2:
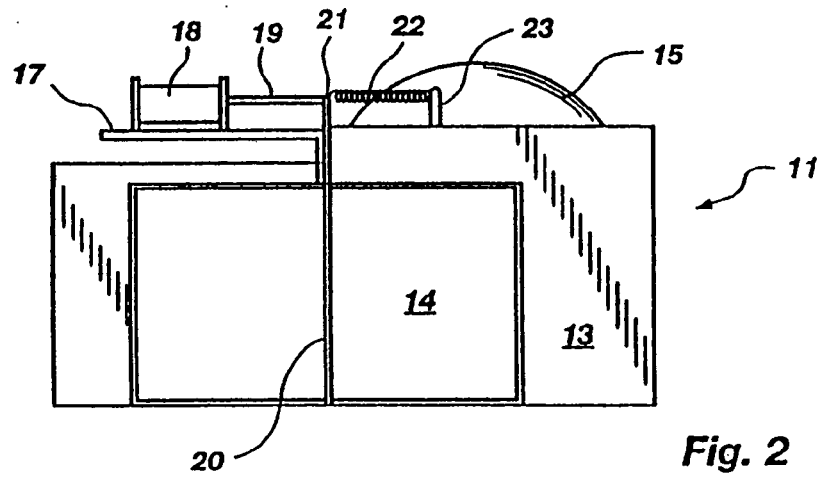
FIG. 2 is a side elevation view of the fluid chamber portion of the apparatus in FIG. 1.
Figure 3:
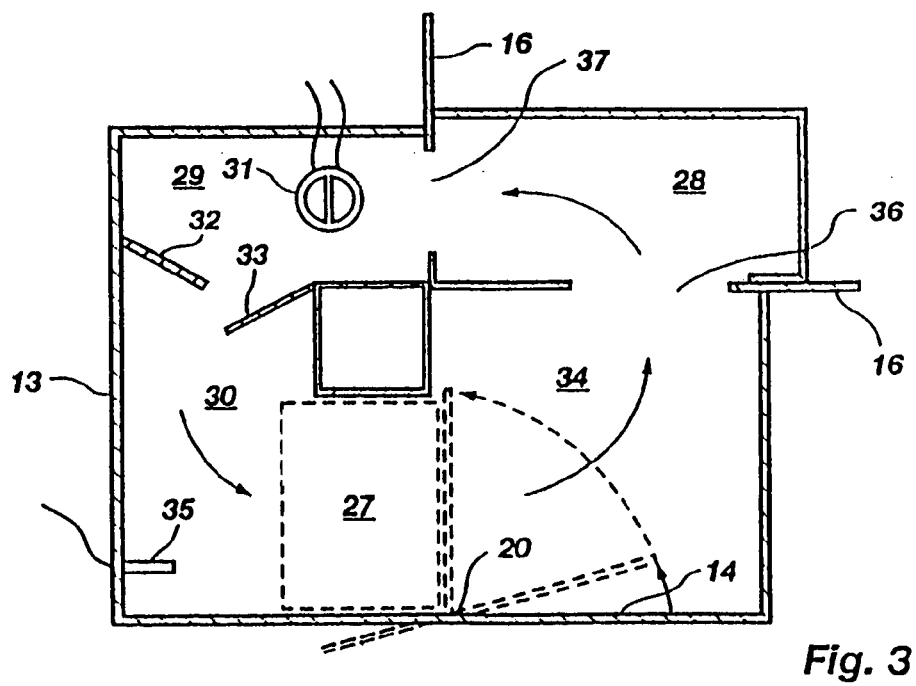
FIG. 3 is an interior plan view of the fluid chamber portion of the apparatus illustrated in FIG. 1.

As shown in FIGS. 2 and 3, the interior of chamber 11 is sectioned off into four main compartments. The blower compartment 28 is formed of the blower housing 15 and the blower mounting plates 16. The entirety of blower compartment 28 is filled with the fan and shaft portions of a blower as has been described above. The blower can be any of a number of well-known designs, as has been described above, and has therefore been omitted from FIG. 3 for purposes of clarity. It is sufficient for the present invention to understand that the fan located in blower compartment 28 draws fluid into the blower compartment 28 through inlet opening 36 and pushes the fluid out of exit opening 37.

It is preferred that the fluid be driven by the blower at a rate of at least 75 cubic feet per minute. It is important however, in regard to the present invention, to realize that the fluid located in chamber 11 only contacts the fan and a portion of the drive shaft of the blower, the blower motor itself being located outside of the blower housing 15 so as avoid any contact thereof with fluid in the chamber 11. This is important since it is critical to the speed of operation of the invention to minimize the material which contacts the fluid inside the chamber 11 so as to minimize the thermal mass of material which must be heated and/or cooled thereby during the cycling process. By minimizing the thermal mass which must be heated or cooled by the fluid, the response time necessary to bring the contents of chamber 11 to a uniform temperature is greatly diminished.

Fluid exiting blower compartment 28 through outlet opening 37 enters heating compartment 29. Fluid passing into heating compartment 29 must pass by heating coils 31. If heating coils 31 gets hotter than the fluid passing into heating compartment 29, the fluid will become heated thereby as it is forced through the compartment. The heating coil is preferably a 1,000 watt (125 VAC) nichrome wire coil wound around a microsupport. However, any heating unit suitable for heating the type of fluid present in the chamber may be used. The particular heating coil of embodiment of FIGS. 1-3 is manufactured by Johnstone Supply, of Portland, Oreg.

The heating coil is activated by an output relay included in the controller 12. The preferred relay is a 25 A, 125 VAC solid state relay manufactured by Omega Engineering Inc. of Stanford, Conn. as Model No. Omega SSR 240 D25.

Fluid passing through heating compartment 29 becomes incident on baffles 32 and 33 before passing into the reaction compartment 30. Baffles 32 and 33 tend to break up any laminar fluid flow and generate turbulence therein to effectively mix the fluid so that it arrives in reaction compartment 30 at an homogenous temperature.

Thermocouple sensor 35 provides an electrical input signal to controller 12 which corresponds to the fluid temperature in the reaction compartment 30. Temperature monitoring during operation of the thermal cycling device 10 is preferably achieved by a 30-gauge iron-constantan "J-type" thermocouple. The controller uses this information to regulate the heat coil 31 according to the predetermined temperature versus time profiles programmed therein and to actuate solenoid 18, as will be explained momentarily.

The fluid passing from the reaction compartment 30 to the return air compartment 34 must pass through sample compartment 27 (as shown in dashed lines). Sample compartment 27 will also be explained momentarily.

The fluid in return compartment 34 has been slightly cooled due to the heat transfer therefrom into samples located in sample compartment 27. The fluid in return compartment is drawn through inlet opening 36 into blower compartment 28 where it is again forced, by action of the fan, out through outlet opening 37 into the heating compartment 39. Thus, the fluid chamber 11, when operating with vent door 14 closed, is a closed loop fluid chamber which continuously recirculates the fluid along a closed loop path through each compartment thereof in order to bring the contents therein to a uniform temperature. Continuous circulation of the air in the air chamber 11 allows the samples in sample compartment 27 to be brought to a predetermined temperature as quickly as possible and then to be held at that temperature, if desired.

When the device 10 must be used to not only heat material located the reaction compartment 27, but also to subsequently cool these materials as quickly as possible to a temperature at or above the ambient fluid (air) temperature, the controller 12 can be programmed to actuate solenoid 18 to cause vent door 14 to open and allow large quantities of ambient fluid to immediately flood the compartment 11 while heated fluid therein simultaneously escapes.

Deactivation of the heating coil 31 while continuing activation of the blower with vent door 14 open, will draw ambient fluid into return compartment 34 and from there into the blower compartment 28. The blower will then push this ambient fluid through heating compartment 29 where it will pass directly into reaction compartment 30 without being heated by coil 31. The ambient fluid then passes through the sample compartment 27 and escapes out of chamber 11 through the vent door 14. Due to the minimum thermal mass of material located in chamber 11, and the action of the blower fan, vast quantities of ambient fluid will be forced past the sample compartment 27, and from there out of the chamber 11. Thus, rapidly cooling of samples or material located in the reaction compartment 27 is obtained.

The sample compartment 27 is sized so as to allow a plurality of samples, such as hollow elongate glass tubes containing a sample therein, to be easily located in a space apart orientation so that fluid may pass evenly around each sample. If desired, sample compartment 27 may be sized and configured so as to allow insertion of a rack, basket, or the like which has been configured so as to accept a plurality of samples in uniform spaced apart configuration so as to simplify loading the samples into the sample chamber 27.

Access to sample compartment 27 is accomplished by rotation of the vent door 14 to its open position. Once the vent door 14 is rotated to approximately 90 degrees from it's closed position, the sample compartment easily accessible therethrough. Also, as can be seen, rotation of vent door 14 approximately 90 degrees from its closed position causes return fluid compartment 34 to be substantially closed off from reaction compartment 30. Thus, when the device 10 of the present invention is in a "cooling" mode, ambient fluid enters directly into return fluid compartment 34 and is forced through the blower compartment 28, heating compartment 29, reaction compartment 30, and sample compartment substantially along the same path as the closed loop fluid flow path described above. The fluid is then forced out of the air chamber 11 and prevented from passing back into air return compartment 34 by the positioning of the vent door 14 between the sample and the compartment return fluid compartment 34.

Thus, the vent door 14 not only allows ambient fluid to enter the chamber 11, it can also prevent the fluid from recirculating in a loop fashion through the chamber 11. Instead, fluid forced pass through the sample compartment 27 and then out of the chamber 11 to aid in the rapid cooling of the sample contents and chamber 11.

When the device 10 of the present invention is used for cyclic DNA amplification, repetitive cycling through temperature versus time profile is required. Samples containing reaction mixture for the polymerase chain reaction generally must be cycled approximately times through a temperature versus time profile which corresponds to the denaturation, annealing and elongation phases of the amplification process.

The device 10 of the present invention, due to its lower overall thermal mass, is capable of cycling samples through significantly shortened temperature versus time profiles compared to the prior art. The DNA amplification application the embodiment FIGS. 1-3 can pass through temperature versus time profile cycle in 30-60 seconds (see FIG. 5). This same cycle using prior art devices would take approximately 5-10 times longer. These low cycle times have proven also increase yield and specificity the polymerase chain reaction over prior art cycling.

EXAMPLE 1

The polymerase chain reaction was run in a 10 µl volume with 50 ng template DNA, 0.5 mM of each deoxynucleotide 500 mM of each oligonucleotide primer in a reaction buffer consisting of 50 mM Tris-HC1 (pH 8.5 at 25° C.), 3.0 mM magnesium chloride, 20 mM HC1, and 500 µg/ml bovine serum albumin (5). Thermos aquatics polymerase (0/4 units Taq polymerase—Stratagene™) was added, the samples placed in 8 cm long, thin-walled capillary tubes (manufactured by Kimble Kimax 46485-1), and the ends fused with a laboratory gas burner so that an air bubble was present on both ends of each tube.

The capillary tubes were then placed vertically in a holder constructed of 1 mm thick "prepunched perfboard" (manufactured by Radio Shack). The mixture was cycled 30 times through denaturation (90-92° C.), annealing (50-55° C.), and elongation (72-75° C.) for the times indicated the temperature versus time profile of FIG. 5. Temperature monitoring of the capillary tubes was done with a miniature thermocouple (IT-23, Sensortek, Clifton, N.J.) placed in 10 ul of deionized water and connected to a thermocouple monitor (BAT-12, Sensortek). Amplification products were fractionated by electrophoresis on a 1.5% agarose gel. Good results were obtained.

Due to the fact that the device 10 the present invention cycles air as the heat transfer medium instead water, it has the advantage that heat transfer occurs through a low heat capacity medium (air) which can be warmed very rapidly.

Figure 5:
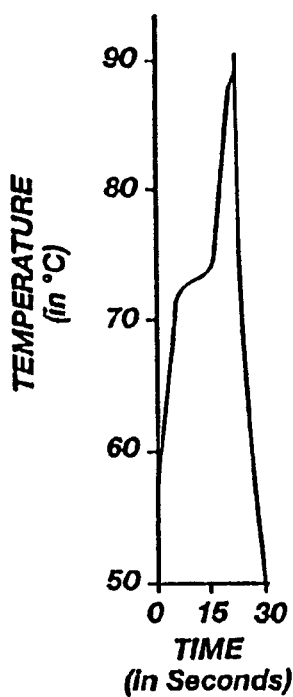
FIG. 5 shows an optimized temperature versus time profile for a polymerase chain reaction using the thermal cycling device of the present invention.

The response time for sample cooling is very fast due to the use of thin walled glass capillary tubes for holding samples, instead of plastic microfuge tubes as has been done in the past with prior art processes, and by minimizing the thermal mass of material inside the chamber 11 (see FIG. 5).

Such response times can allow for optimization of the denaturation and annealing, and elongation steps in the polymerase chain reaction, in terms of time and temperature.

Further, shortened "ramp" times are obtained, i.e., the time required to bring the temperature of the sample from one temperature level to the next temperature level corresponding to phases in the amplification process is shortened. This decreases the time required for a complete amplification, as well as allowing specific study of annealing, denaturation and enzyme kinetics within a polymerase chain reaction protocol.

Figure 4:
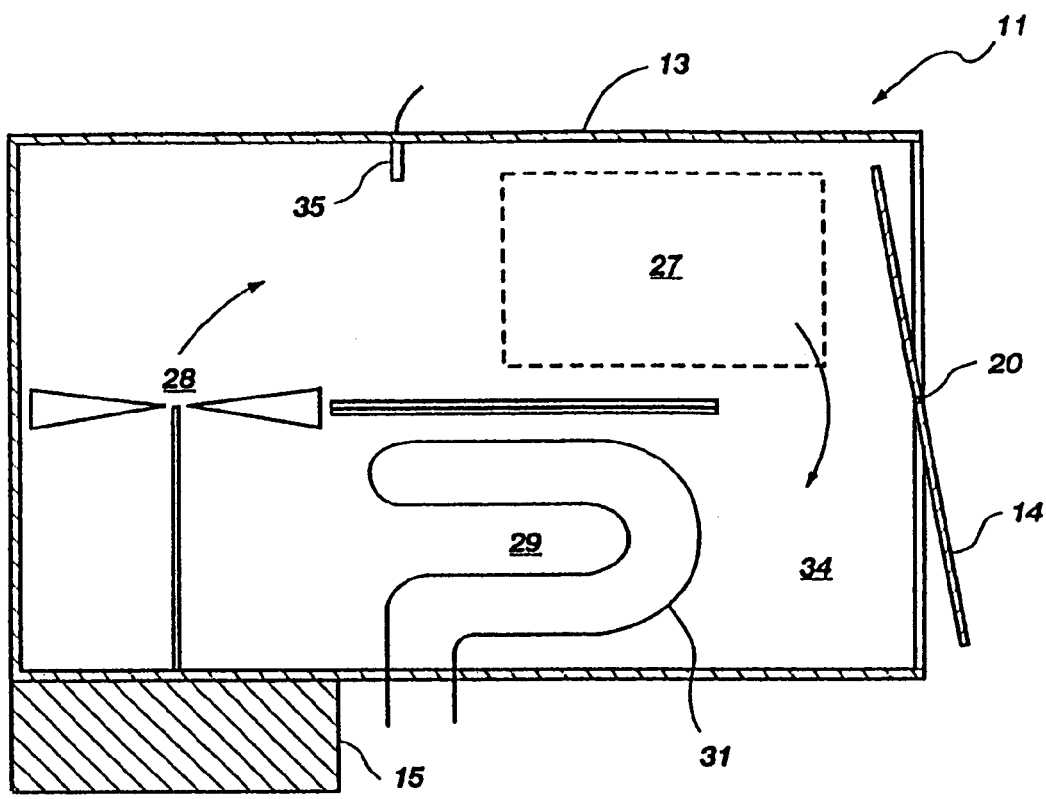
FIG. 4 shows and interior plan view of the fluid chamber of an another embodiment of the present invention.

The baffles 32 and 33 (as shown in FIG. 3) may be used if desired to achieve adequate temperature homogeneity within the sample compartment 27. As shown in this embodiment, baffles 32 and 33 decrease the temperature variation in the reaction compartment 30 from about 10° C. to about 2° C. If desired, further (or more complicated) baffles may be used to further decrease the temperature variation reaction compartment 30. Alternately, as shown in FIG. 4 the fan may be positioned downstream from the heating coil 31, but before the sample compartment 27 to achieve more uniform mixing.

Figure 6:
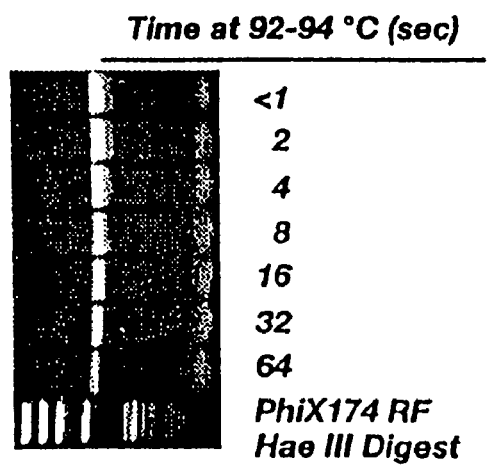
FIG. 6 shows graphically the effect of annealing time on polymerase chain reaction specificity and yields using the thermal cycling device of the present invention.

Amplification products obtained through the use of apparatus 10 are qualitatively and quantitatively similar to those obtained through the manual water bath cycling method. However, advantages in specificity and yield are possible with rapid thermal control of the reaction mixture. FIG. 6 shows the effect of varying the denaturation time of the temperature versus time profile of FIG. 5 as used with the thermal cycling apparatus 10 of the present invention on DNA amplification yields. The brighter vertical lines each correspond to a particular time at a denaturation temperature. As can be seen, the yield is greatest at the shortest possible denaturation time. Such a rapid response is not possible with prior art systems.

Figure 7:
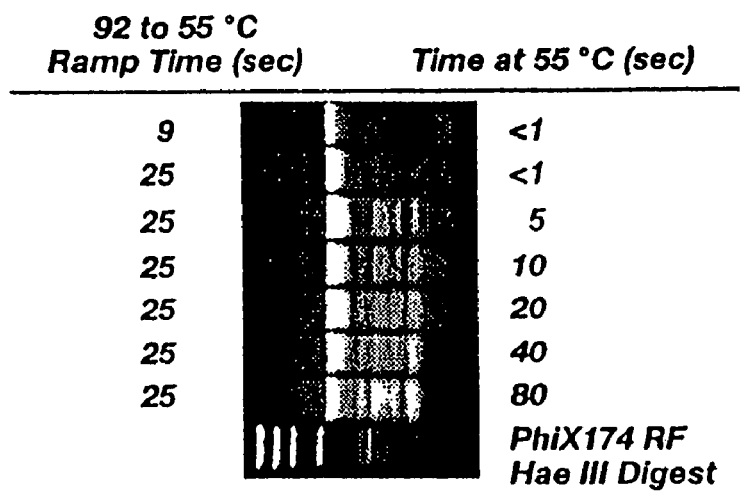
FIG. 7 shows graphically the effect of denaturation time on polymerase chain reaction yields using the thermal cycling device of the present invention.

FIG. 7 shows the effect of the temperature versus time profile of FIG. 5 as used with the thermal cycling apparatus 10 on specificity (i.e., one specific product yield as opposed to a plurality of similar or "shadow" products). As can be seen, the shorter the ramp and annealing time, the greater the product specificity. The rapid temperature response of the apparatus 10 allows improved specificity and yield which is not possible with prior art systems.

As has been shown, by decreasing the thermal capacity (thermal mass) of the apparatus 10, the present invention can markedly decrease the total time required for the polymerase chain reaction. In addition, the use of small samples reduces the amounts of expensive reagents which must be used by up to about 90% thus further reducing the cost of carrying out procedures using present the invention. For example, capillary tubes 108 having inner diameters in the range from about 0.25 mm to about 1.0 mm can desirably be used. In some applications, capillary tubes 108 having inner diameters in the range from about 0.02 mm to about 0.1 mm can also be desirably used.

The apparatus 10 of the present invention is useful for amplifying any source from DNA. Although particular configurations and arrangements of the present invention have been discussed in connection with the specific embodiments of the thermal cycling device 10 as constructed in accordance with the teachings the present invention, other arrangements and configurations may be utilized. For example, various fluids other than air, of generally low thermal mass, may alternatively be used in the device 10.

Figure 8A:
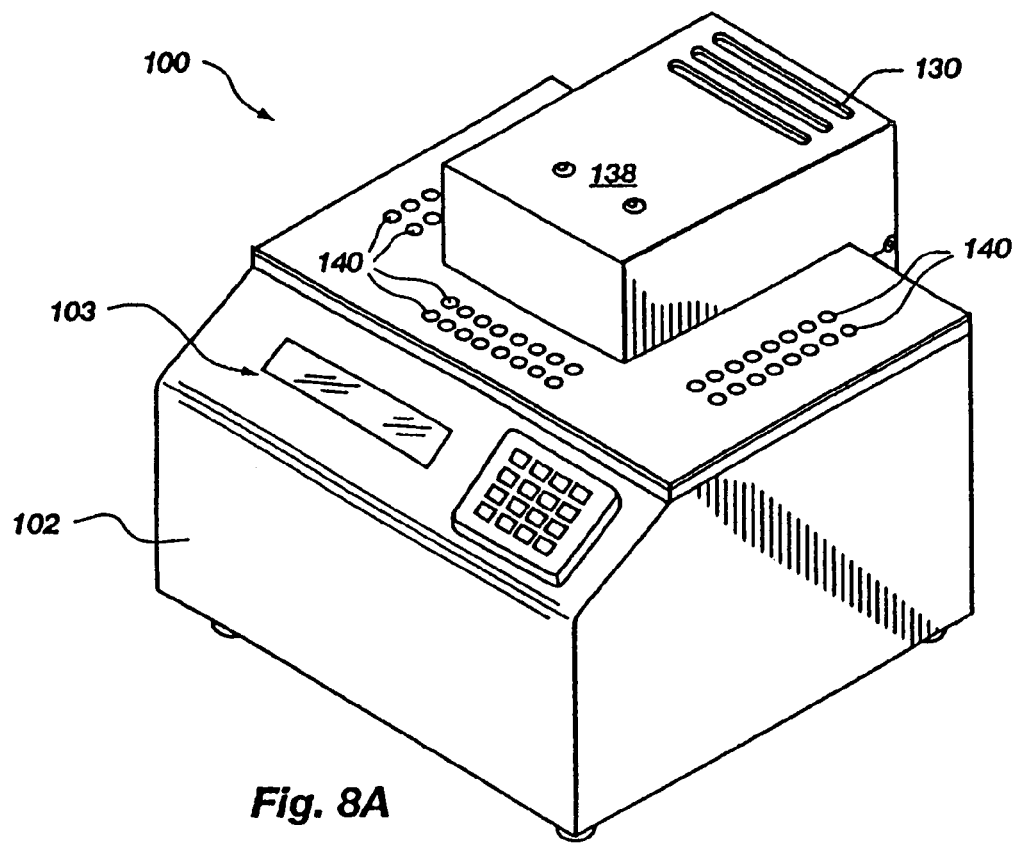
FIGS. 8A-B, which are perspective and elevational cross sectioned views, respectively, of another preferred embodiment of the present invention.
Figure 8B:
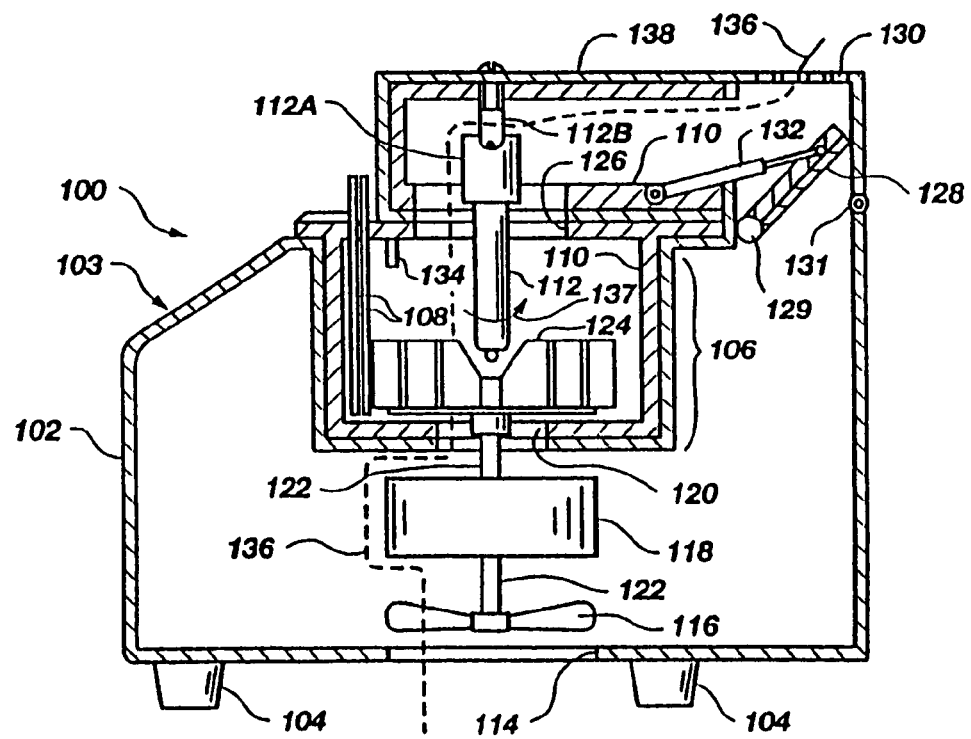
Figure 8C:
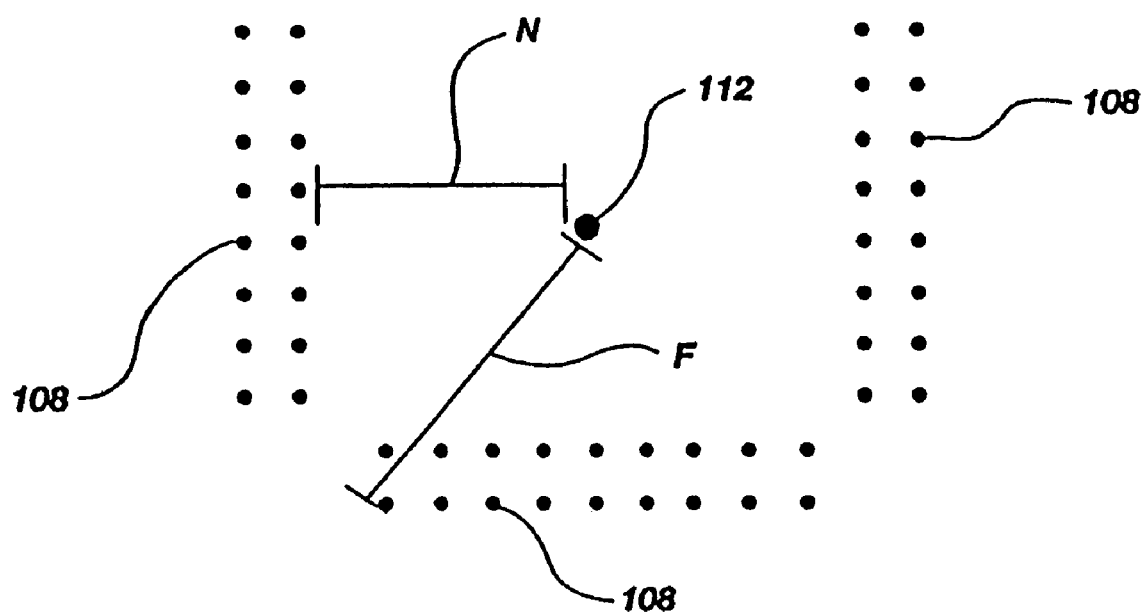
FIG. 8C is a diagrammatic representative of the relationship of the heat producing element and the capillary tubes holding the biological samples in the embodiment illustrated in FIGS. 8A-B.

Another embodiment of the present invention is represented in FIGS. 8A-C. FIG. 8A is a perspective view and FIG. 8B is an elevational cross sectioned view of the additional embodiment. It will be understood that many of the earlier explained components and teachings also have application in the embodiment illustrated in FIGS. 8A-C. Thus, only the pertinent additional information concerning this embodiment will be provided below. Importantly, in the embodiment of FIGS. 8A-C, the heat producing element is adjacent to the biological sample containers allowing faster heating and cooling of biological samples as explained below.

As will be appreciated shortly, the apparatus of FIGS. 8A-C provides even greater improvement over the prior art in the speed at which thermal cycling can be carried out, e.g., 15 or 30 cycles of DNA amplification in 30, 15, 10 to 5, or even fewer, minutes. Furthermore, the apparatus 100 provides better thermal homogenization throughout the samples than previously possible.

Shown in FIG. 8A is the general configuration of the housing 102 of the embodiment. The housing 102 rests on feet 104 (best seen in FIG. 8B) and functions to hold the other described structures in place and to isolate those structures which become hot from the surrounding environment. Included in the embodiment 100 of FIG. 8A are input keys 25 and a display 26 as in the previously described apparatus 10. The previously described control structures can readily be modified or used as a pattern for a control means for use in the embodiment of FIGS. 8A-C.

As shown best in the cross sectional view of FIG. 8B, a sample chamber is designated by bracket 106. A lid 138 connected to the housing 102 by a hinge 131 can be opened to allow access to the sample chamber 106. The sample chamber 106 is preferably cylindrical in shape but can be of any shape or size required by the particular application.

The sample chamber 106 is lined with a black colored foam material 110 whose surface has light absorbing characteristics with the bulk of the thickness of the foam having insulating characteristics. The black foam material can be one which is readily available in the art and one fabricated from a plastic material. The foam 110 is preferably a material which is readily cooled by the air passing there over, i.e., the material has low thermal conductivity and a porous surface.

The dark or black porous surface of the material converts shorter wavelength radiation striking the surface into longer wavelength radiation, i.e., heat, which is radiated into the sample chamber.

The foam 110 functions to thermally isolate the sample chamber from the surrounding air space in the housing and also to convert the light emitted by lamp 112 into thermal energy. The foam 110 can be replaced with other structures. For example, material having black dark, other nonreflective surface, such as a thin sheet of polycarbonate having one surface painted black, can backed by insulative material, such as a fiberglass or foam material. The black or dark surface, which can be painted on a number of different substrates, converts shorter wavelength radiation striking into thermal radiation while the insulative material thermally isolates the sample chamber from the surrounding environment. Thus, using the teachings provided herein, those skilled in the art can utilize many different materials and structures as a lining for the sample chamber.

The lamp 112 is preferably a 500 watt halogen lamp. If appropriate control devices are used, higher power lamps or a plurality of lamps, such as four 500 watt halogen lamps, can be used. A lamp socket 112A is attached to the housing 102 by a support 112B. The lamp 112 is able to very rapidly and uniformly heat the sample chamber 106 the desired temperature. Other sources of heat, i.e. infrared radiation, such as the earlier described nichrome wire element, can also be used within the scope of the present invention.

Represented in FIG. 8B are two thin-walled capillary tubes 108 such as those described earlier. While two thin-walled capillary tubes 108 are shown, the sample chamber 106 can hold many such tubes. The thin-walled capillary tubes 108 have several important advantages over previously used devices as described earlier and, together with the sample chamber 106, function as the one presently preferred example of a means for holding a biological sample.

It will be appreciated that many other structures performing equivalent or similar functions can also be used. The thin-walled capillary tubes 108 are preferably left partially extending out the sample chamber through apertures 140 for ease of access but may be completely contained within the sample chamber 106 as may numerous other fluid holding structures which are suited to particular applications. The preferred thin-walled capillary tubes 108 have a capacity of about 10 μl. As will be understood, the volume of the sample should be keep small, and the surface area of the sample holding structure relatively large, and together they should present a relatively small thermal mass. It is also preferred that the sample holding structure contain a volume anywhere from about 0.1 μl to about 10,000, μl but those skilled in the art will appreciate that other volumes of samples can also be used within the scope of the present invention if the different thermal mass of the structure is considered.

The lamp 112 and the insulative foam 110 together provide rapid and uniform heating of the sample contained in the thin-walled capillary tubes 108 and the air contained within the sample chamber 106. A thermocouple 134 is included within the sample chamber 106 to sense the temperature within the chamber and is used to maintain the desired temperature within the sample chamber as earlier described.

The thermocouple 134 is preferably one available in the art whose thermal response substantially matches the thermal response of the biological sample and the container holding the same. Such thermocouples can be commercially obtained from sources such as Idaho Labs which manufactures a line of thermocouples referred metal sheathed, J-type thermocouples. The matching of the thermal response of the thermocouple to that of the biological sample and container can be preferably carried out by inserting micro thermocouple, such as the model IT-23 thermocouple available from PhysiTemp as known in the art, into a typical biological sample being held by the chosen container and subjecting the sample and the thermocouple under test to the same temperature changes. The thermocouple under test, or some external criteria, can be changed until the thermal response of the thermocouple suitably matches the thermal response of the sample and its container.

The arrangement represented in FIG. 8B provides more uniform heating and cooling of the sample than previously available devices. In previously available devices, transfer of heat throughout the sample is carried out by convection through the sample. Convection induced movement of the sample within whatever structure is used to hold the sample is caused by temperature gradients or differences in the generally small biological samples (e.g., 10-100 μl).

The effect of temperature gradients within the sample become more pronounced and more difficult to control as the cycle time for a sample decreases. The existence of uneven temperatures within a sample, and particularly the reliance on "mixing by convection" within the sample by the prior art devices, generally increases the cycle time for a sample and likely has deleterious effects on the biological sample. The apparatus 100 is capable of providing heating and cooling such that thermal differences within a 10 μl sample are maintained at not greater than ±1° C. at all times during a 30 second cycle.

In order to promote uniform heating and cooling, it is preferred that the thin-walled capillary tubes 108 be at least somewhat uniformly spaced from the heat source, for example, lamp 112 in apparatus 100. FIG. 8C provides a diagrammatic top view of the lamp 112 and the plurality of thin-walled capillary 100 tubes 108 arranged in the apparatus 100 represented in FIGS. 8A-B.

In the arrangement represented in FIG. 8C, the thin-walled capillary tubes 108 which are farthest from the lamp 112 (as indicated by line F) are preferably no more than substantially 40%, and more preferably no more than substantially 25%, farther from the lamp 112 than the distance between the lamp 112 and those thin-walled capillary tubes 108 which are closest to the lamp 112 (as indicated by line N). For example, the distance indicated by line N can be about 7.3 cm while the distance indicated by line F can be about 8.5 cm.

It will be appreciated that the arrangement of the thin-walled capillary tubes 108 can be other than that represented in the figures, for example, circular or semi-circular. Moreover, it will appreciated that the point from which to measure the distance between the heat producing element and the sample containers will vary as the type and size of the heat producing element varies. For example, the heat producing element may comprise a plurality of lamps or electric resistive elements which vary in shape and size. In some embodiments, it may also become important to consider the distance from the sample chamber wall the sample containers are positioned. In the illustrated embodiment, the apertures 140 (see FIG. 8A) function as a means for holding the sample containers but other structures performing equivalent functions can also be used in accordance with the present invention.

The apparatus 100 also cools the samples contained in the capillary tubes 108 very rapidly and uniformly. In order to cool the sample chamber 106, air from outside the housing 102 is draw into the interior of the housing through a lower housing portal 114 by a fan 116 which is connected to a motor shaft 122 driven by a motor 118. Since rapid cooling of the sample chamber is desired, it is preferred that the combination of the motor 118 and the fan 116 be able to move sufficient volumes of air into the sample chamber 106 and then disperse that air inside the sample chamber 106, as will be explained shortly. Arrangements other than the motor 118 and fan 116 illustrated in FIG. 8B can also be used within the scope of the present invention.

The use of air as the thermal transfer medium, in contrast to other gases and liquids, has the advantages of being inexpensive, readily available, easily mixed, and never making a mess. In the case of the described embodiments, the high surface area-to-volume ratio of the sample containing capillary tubes provides for rapid thermal transfer using air as the thermal transfer medium.

During cooling portions of the thermal cycle, the action of the fan 116 draws ambient temperature air into the housing 102. A vent door 128, articulating on hinge 129, is provided. The vent door 128 is automatically opened by way of a solenoid 132 so that the interior of the housing 102 is sealed off from the upper housing portal 130. In some embodiments, the solenoid 132 is preferably replaced by a stepper motor as is known in the art. The use of a stepper motor allows the vent door 128 to be accurately and incrementally opened and closed in accordance with the needs for heating and cooling the samples. Those skilled in the art will be able to derive an appropriate control mechanism for use with a stepper motor, for example an SC-149 stepper motor controller (available from Alpha Products) as known in the art, using the information set forth herein.

Due to the arrangement of the lower sample chamber portal 120 and the larger cross sectional area and position of the upper sample chamber portal 126, room temperature air is moved into the sample chamber 106 and is dispersed and mixed within the sample chamber 106 by a paddle 124 which is connected to the motor shaft 122. The paddle 124 should rotate at a relatively high rate, for example, fast enough to create air velocities of around preferably about 250, more preferably 500, and most preferably 1000 meters per minute within the sample chamber 106. With the paddle 124, which can be a single or a multivane paddle, rotating at a high speed, air is moved, or drawn, into the sample chamber 106 and vented out of the sample chamber 106 following the path indicated by the dashed line 136. The rotation of the paddle 124 also promotes mixing of the air entering the sample chamber 106 and ensures the most efficient transfer of thermal energy from the surfaces of the thin-walled capillary tubes 108 to the air passing through the sample chamber 106. It will be appreciated that structures other than those illustrated herein can perform equivalent functions.

As the solenoid 132 is actuated to open the vent door 128, all of the room temperature air moved into the sample chamber 106 is exhausted through a sample chamber upper portal 126 and then through the upper housing portal 130 carrying the heat from the sample chamber 106 to the surrounding atmosphere. The rapid mixing of the air that passes through, and is disbursed in, the sample chamber 106 results in rapid and uniform cooling of the samples.

EXAMPLE 2

Figure 9A:
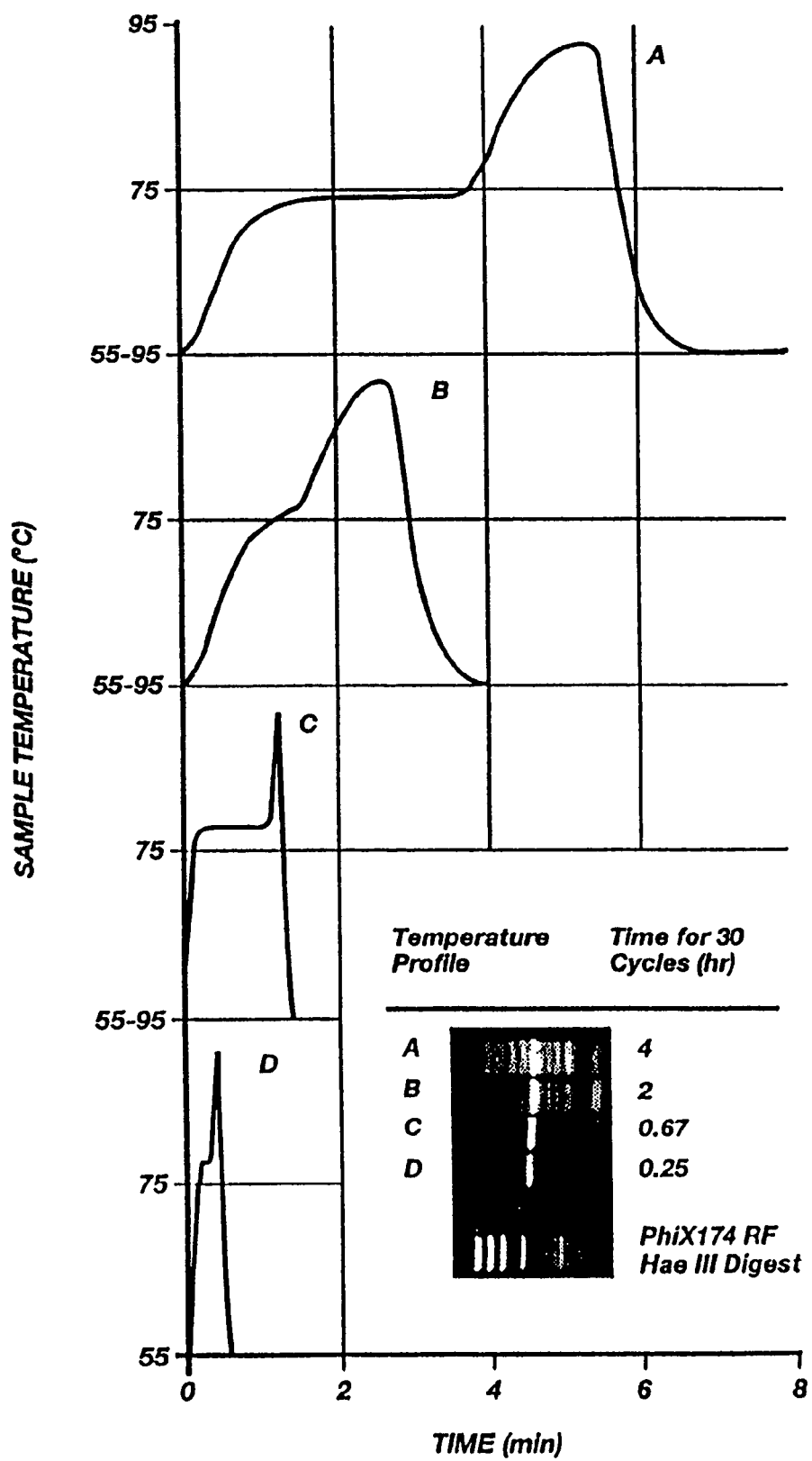
FIG. 9A shows the results of four different temperature/time profiles (A-D) and their resultant amplification products after thirty cycles (A-D).

FIG. 9A shows the results of four different temperature/time profiles (A-D) and their resultant amplification products after thirty cycles (A-D). The profiles A and B in FIG. 9A were obtained using a prior art heating block device using the prior art microfuge tube. As can be seen in FIG. 9A, the transitions between temperatures are slow and many nonspecific bands are present in profiles A and B. Profile B shows improvement in eliminating some of the nonspecific bands (in contrast to profile A) by limiting the time each sample remains at each temperature thus indicating that shorter times produce more desirable results.

Profiles C and D were obtained using the apparatus of FIGS. 8A-B. As can be seen in FIG. 9A, amplification is specific and, desirably, even though yield is maximal in C (60 second elongation) it is still entirely adequate in D (10 seconds elongation).

The optimal times and temperatures for the amplification of a 536 bp fragment of globin from human genomic DNA were also determined. Amplification yield and product specificity were optimal when denaturation (93° C.) and annealing (55° C.) less than 1 second. No advantage was found to longer denaturation or annealing times. The yield increased with longer elongation times at (77° C.) but there was little change with elongation times longer than 10-20 seconds. These unexpected results indicate that the previously available devices used for DNA amplification are not maximizing the conditions needed to optimize the physical and enzymatic requirements of the reaction.

Further information can be obtained from: Wittwer, Carl T., Marshall, Bruce C., Reed, Gudrun B., and Cherry, Joshua L., "Rapid Cycle Allele-Specific Amplification with Cystic Fibrosis $\Delta F_{508}$ Locus, 39 *Clinical Chemistry* 804 (1993) and Wittwer, Carl T., Reed, Gudrun H., and Rire, Kirk M., "Rapid DNA Amplification," THE POLYMERASE CHAIN REACTION 174 (1994) which are both now incorporated herein by this reference.

From the information provided in FIG. 9A, it can be seen that the embodiments of the present invention subject the samples placed therein to rapid thermal cycling wherein the temperature of the sample is increased and decreased at a rate preferably at least as great as 0.5° C./second. In the case of the present invention carrying out the polymerase chain reaction, the temperature change is preferably carried out over an approximate range of between 30° C. to 50° C. It is preferred that the thermal cycles be carried out quickly enough to complete at least thirty thermal cycles in forty minutes and more preferably complete thirty thermal cycles in twenty minutes and most preferably complete thirty thermal cycles in ten minutes.

The apparatus 100 more preferably increases and decreases the temperature of the sample at a rate at least as great as 1.0° C./second and even more preferably at a rate at least as great as 4.0° C./second and most preferably at a rate at least as great as 10.0° C./second. Critically the biological sample, not just the surrounding medium and/or the sample container, must undergo the specified thermal change. The previously available devices, while having the drawback of not able to perform thermal changes as rapidly as the present invention, also did not recognize the problem of changing the temperature of the sample, not just the temperature of the surrounding medium and container rapidly and uniformly.

Figure 9B:
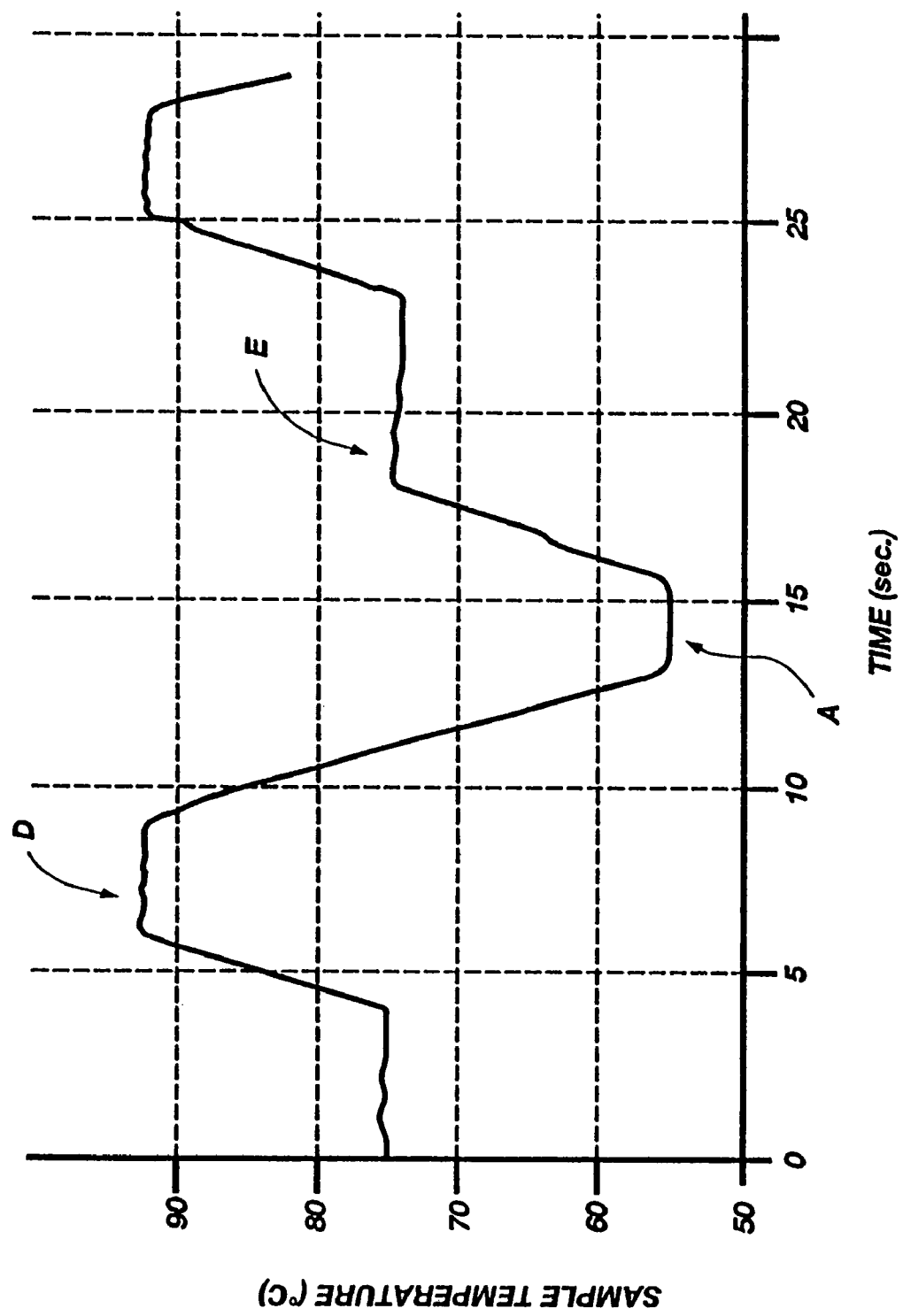
FIG. 9B shows a cycle of another preferred temperature/time profile used by the present invention.
Figure 9C:
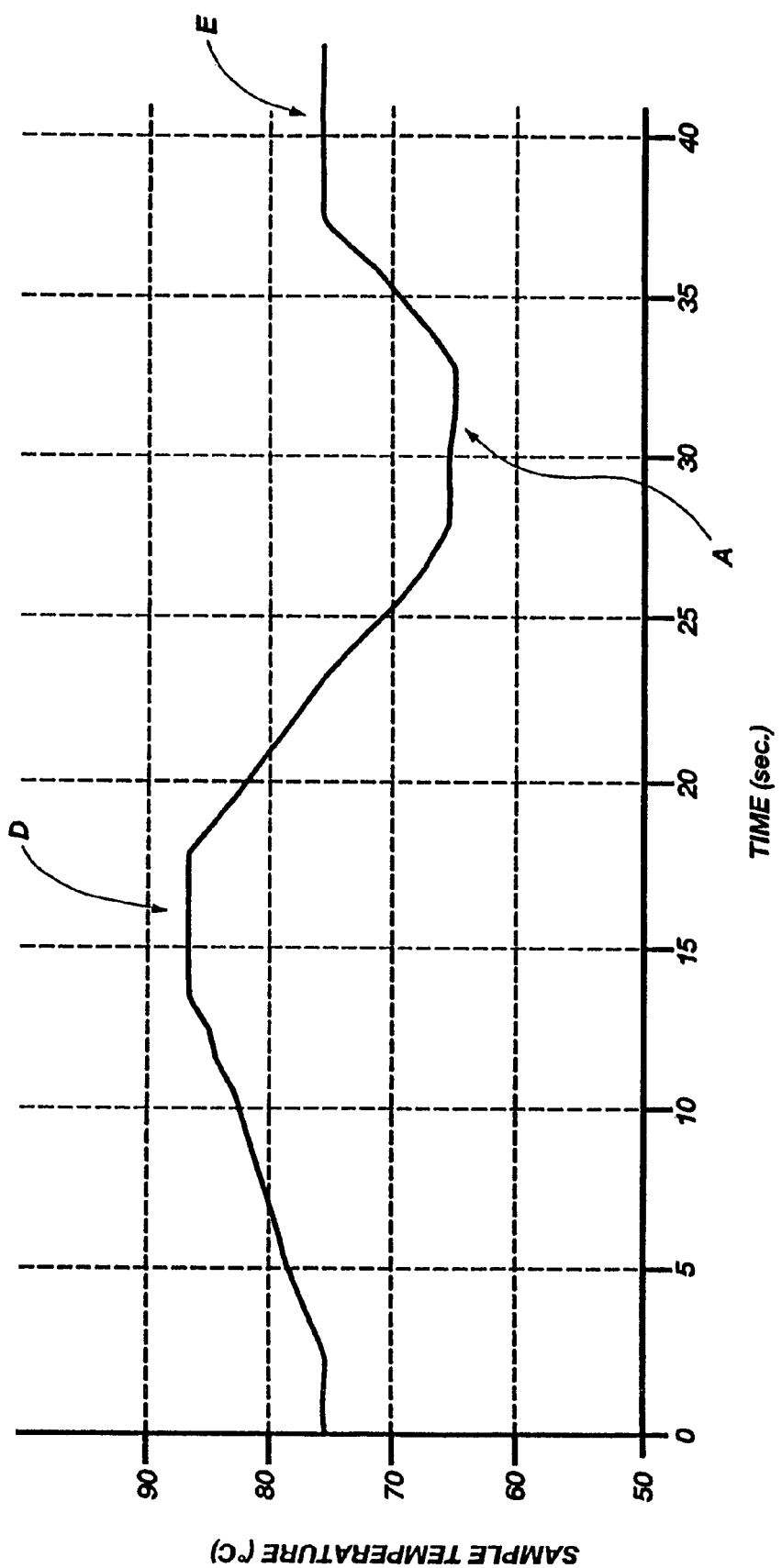
FIGS. 9C-G show exemplary cycle of other preferred temperature/time profiles used by the present invention.
Figure 9D:
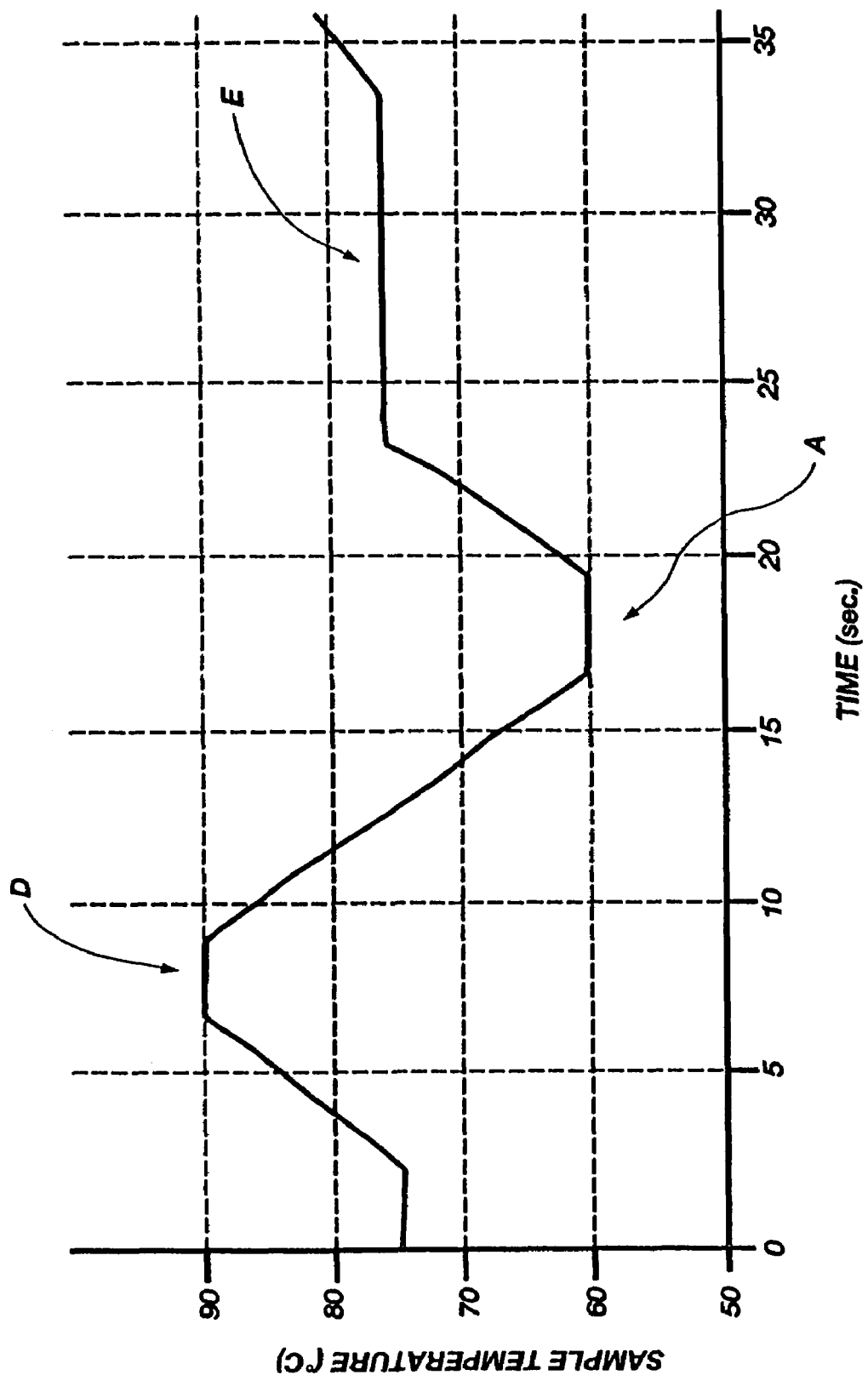
Figure 9E:
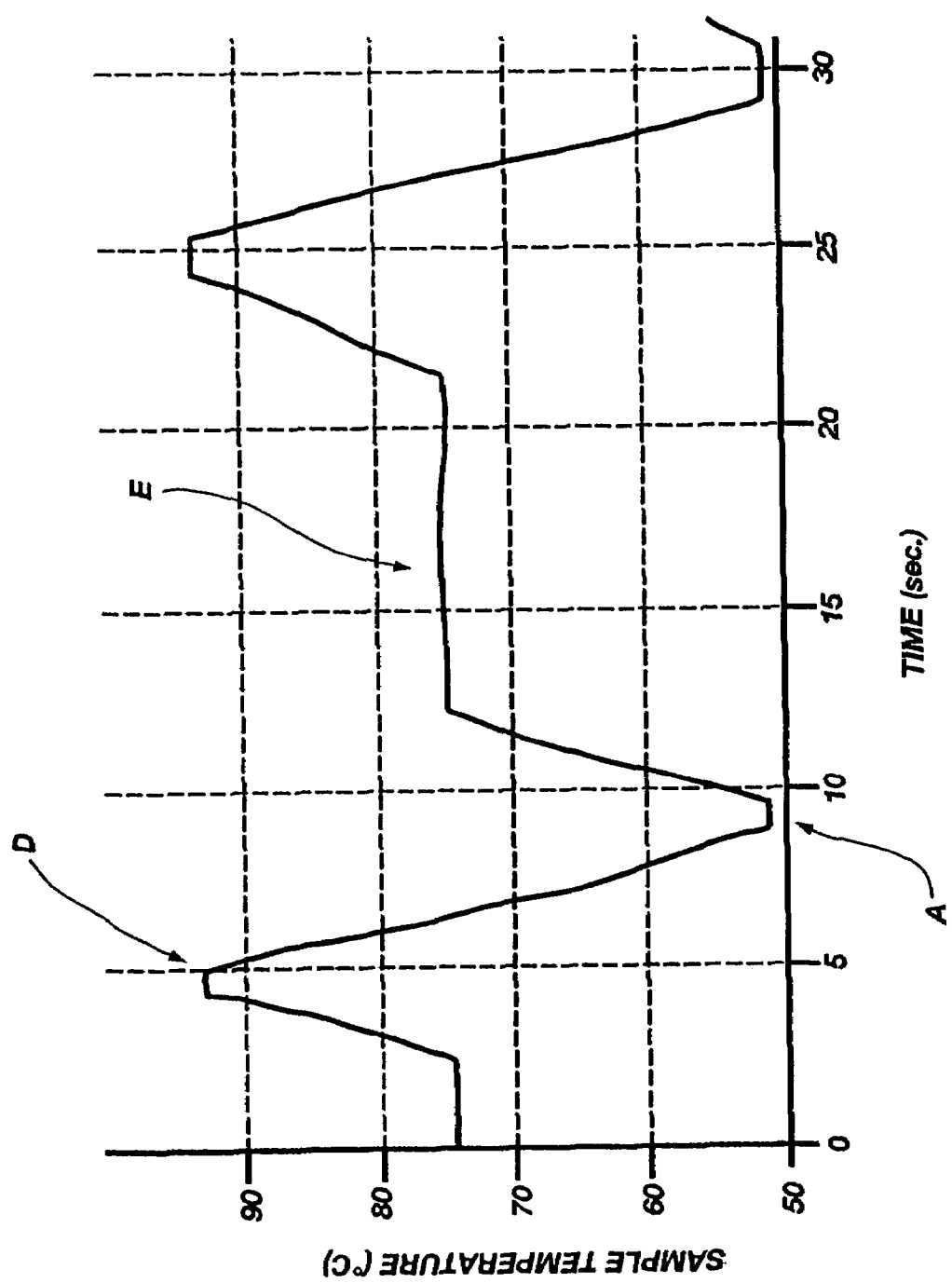
Figure 9F:
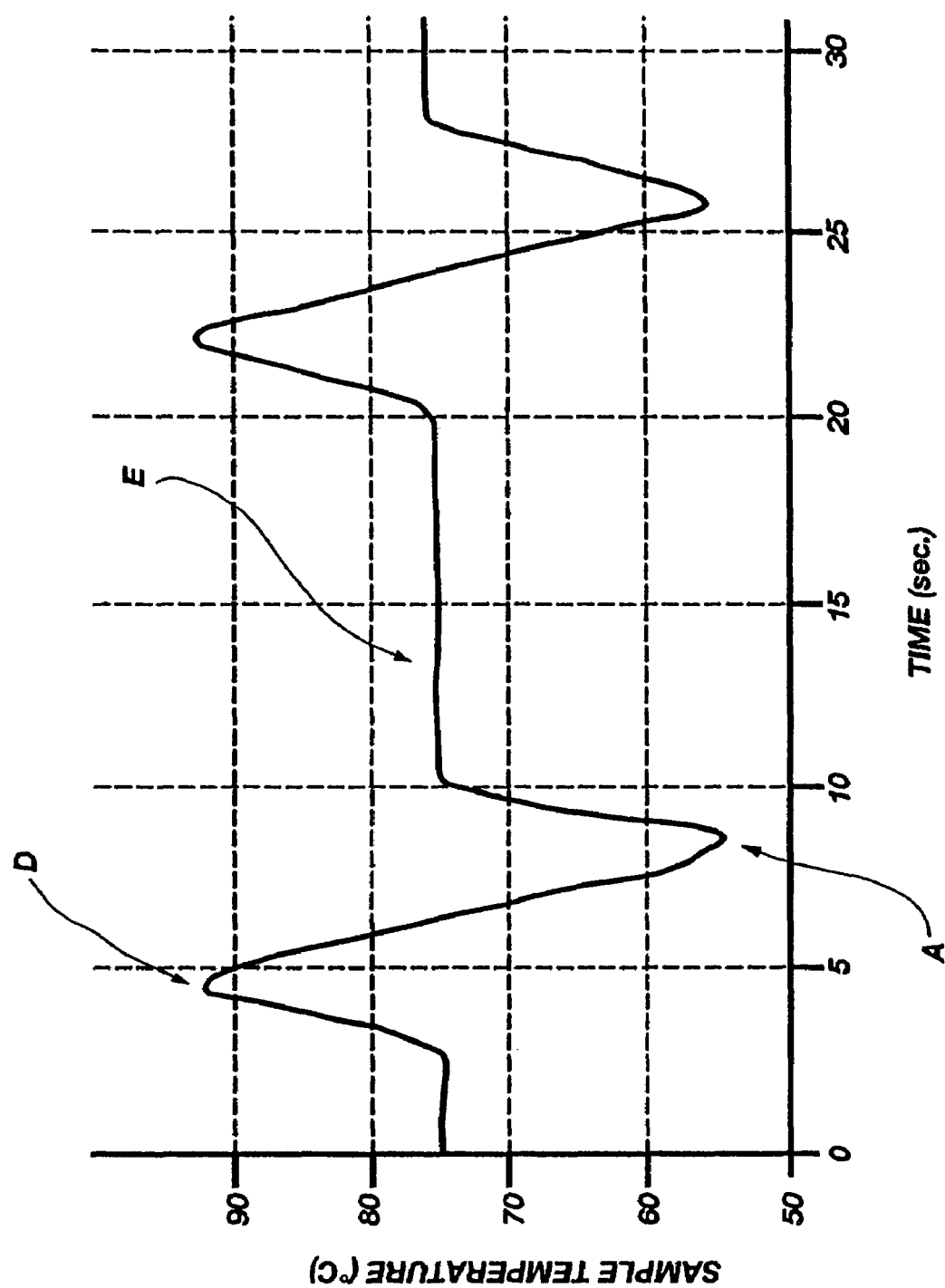
Figure 9G:
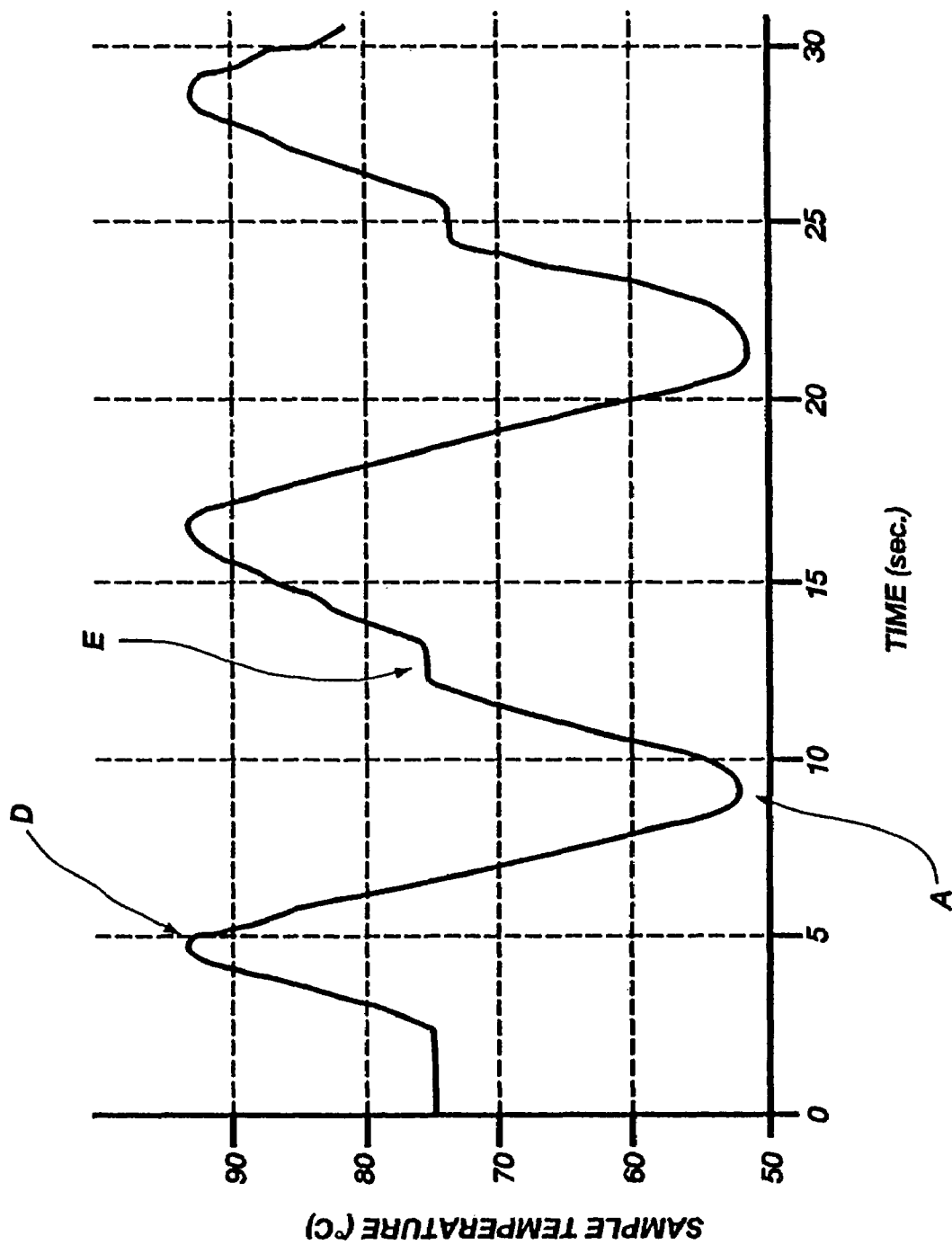

Referring now to the chart of FIG. 9B, the method of the present invention can desirably achieve thermal cycling preferably at a rate at least as great as 10° C./sec., and more preferably at a rate at least as great as 20° C./sec., over a temperature range of greater than about 20° C., more preferably over a temperature range of greater than about 30° C., and most preferably over a temperature range of about 40° C. FIG. 9B shows the temperature in ° C. of the biological sample, not just the surrounding air or container, as the biological sample undergoes the thermal cycle. FIG. 9B shows a PCR sample beginning at about 74° C. and being heated to a denaturation temperature, indicated at D, of about 92° C. for 2 seconds. The sample is then cooled to an annealing temperature, indicated at A, of about 55° C. for two seconds. The transition between the denaturation temperature and the annealing temperature covers a range of 37° C. in just under 4 seconds providing a rate at least as great as 10° C./sec. The sample is then warmed to an extension temperature of 74° C. for five seconds as indicated at E in FIG. 9B. The cycling of the sample through the denaturation temperature, the annealing temperature, and the extension temperature is repeated thirty time or as many times as desired.

FIGS. 9C-G show exemplary cycles of other preferred temperature/time profiles which are achieved by the present invention. It will be understood that those skilled in the art can alter the represented temperature/time profiles to carry out specific processes in accordance with the present invention. Those skilled in the art will also appreciate that the previously available devices and methods, such as devices which conduct heat to and from the sample via a solid or liquid, cannot provide, and do not suggest or teach, the temperature/time profiles described herein. Furthermore, it will be appreciated that the previously available devices and methods utilizing air and the transfer medium, for example previously available chromatographic ovens, cannot provide, and do not suggest or teach, the temperature/time profiles described herein.

Figure 10:
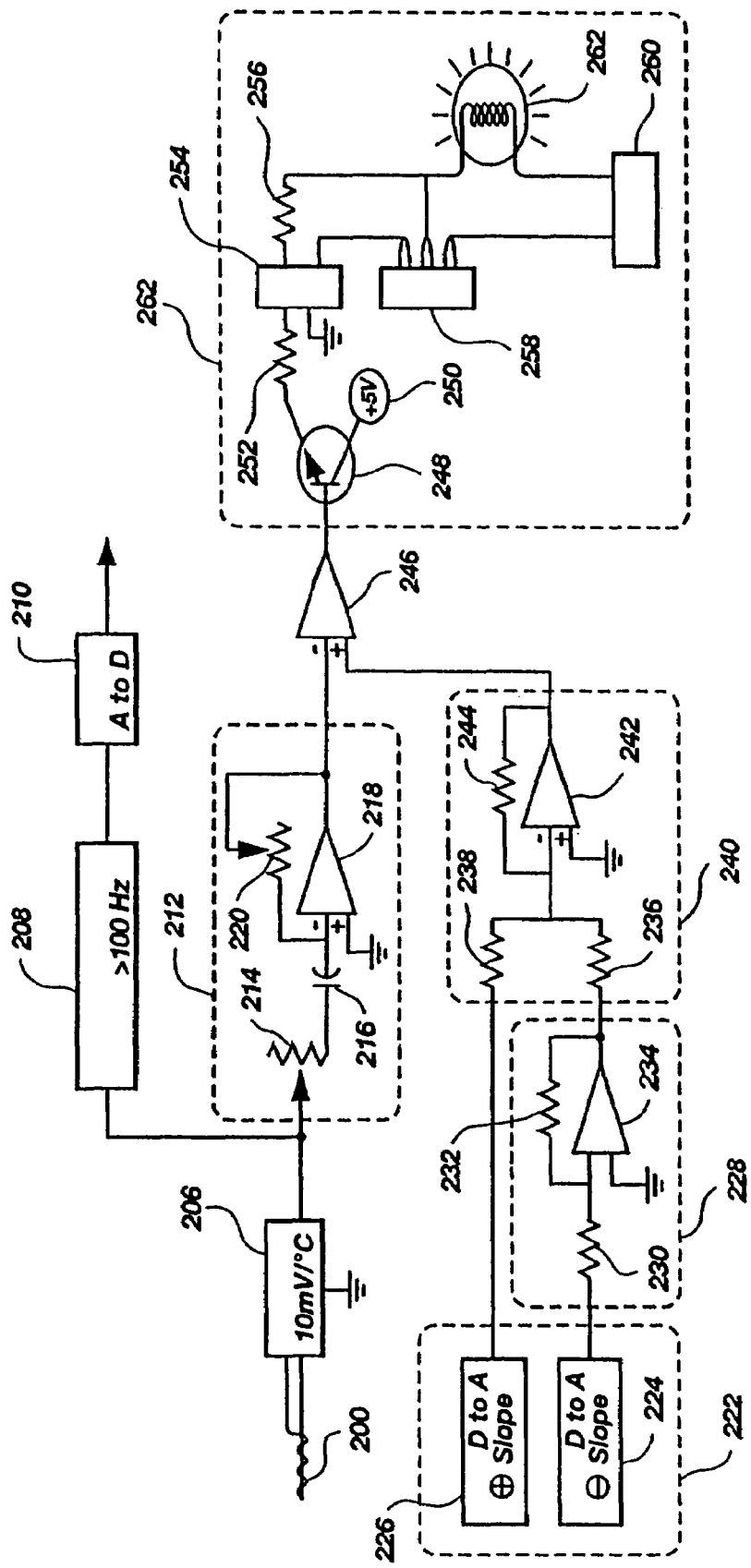
FIG. 10 provides a block diagram of a temperature slope control circuit in accordance with the present invention.

In order to provide the fastest thermal cycling time, it is preferred that the lamp (112 in FIGS. 8A and 8B) be rated at 2000 watts or a plurality of lamps be included which provide similar output. It is also preferred to include a temperature slope control circuit which is represented in FIG. 10 in conjunction with an A-bus controller/acquisition system using an 8052 micro controller board with a clock and high level program interpreter available from Alpha Products model no. SP-127) Darian, Conn. Exemplary programming code used connection with the described microcontroller is included in the Programming Code Appendix attached hereto and incorporated herein. The programming code provided the Appendix is a BASIC52 file for serial downloading into the microcontroller and provides exemplary temperature slope control during thermal cycling. Use of the 2000 watt heat producing device and the describe control structures allows rates of 20 C/sec. to be desirably obtained.

The preferred arrangement for the temperature slope control circuit represented in FIG. 10 will be explained with the understanding the additional necessary components not explicitly illustrated in FIG. 10 can readily be supplied by those skilled in the art.

The temperature slope control circuit of FIG. 10 includes a thermocouple 200 matched to the sample temperature response as explained earlier. The thermocouple 200 is connected to an integrated circuit 206, which preferably is one known in the art as an AD595, whose output is conveyed to a 4th order low pass filter 208 with a cutoff frequency of 100 Hz and to a 12 bit analog-to-digital converter 210 whose output is used to provide digital display of the temperature.

The output of the circuit 206 is also conveyed to a measured slope circuit 212. The measured slope circuit 212 preferably includes a 353 operational amplifier 218, a 100 KΩ potentiometer 214, a 1 MΩ potentiometer 230, and a 22 μF capacitor. The measured slope circuit 212 outputs a signal to the inverting input of a 353 operational amplifier 246.

A slope set circuit 222 includes a positive slope set digital-to-analog converter 226 and negative slope set digital-to-analog converter 224. The digital-to-analog converters 224 and 226 are preferably 8-bit digital-to-analog converters referred to in the art as DA147. The slope set circuit can preferably receive instructions from another digital device (not illustrated in FIG. 10) such as a personal computer. The output of the slope set circuit 228 is communicated to a summing circuit 240.

The summing circuit 240 preferably includes 100 KΩ resistors 236, 238, and 244 and a 353 operational amplifier 242. The output of the summing circuit 240 is conveyed to the non-inverting input of the operational amplifier 246 and represents the desired slope of the temperature change. The output of the operational amplifier 246 is provided to a transistor 248 contained within a power switching circuit 262.

The power switching circuit 262 includes a 5 VDC supply 250 providing current to the transistor 248. The transistor 248 has its emitter connected to a 3010 circuit 254 by way of resistor 252 which is preferably a 330 QΩ resistor. The 3010 circuit 254 includes an output connected in series with a resistor 256 which preferably is a 180 Ω resistor. A triac 258 is preferably used to control the current delivered to a lamp 262, or other heat producing device, from a source of AC current 260.

The temperature slope control circuit represented in FIG. 10, in cooperation with the other described system components, provides thermal cycling of biological samples as great as 20° C./sec over a temperature range of 30° C., and most preferably over a temperature range of 40° C., with homogeneity being maintained throughout the biological sample.

It will be appreciated that the apparatus described herein can readily be used for many different applications including: polymerase chain reaction processes; cycle sequencing; and, other amplification protocols such as the ligase chain reaction. The present invention also advantageously provides an apparatus for accurately controlling the temperature of samples located in the sample chamber and quickly and accurately varies the temperature of samples located in a chamber according to a predetermined temperature versus time profile.

The present invention may be embodied in other specific forms without departing from its spirit essential characteristics. The described embodiments are to be considered in all respects only as illustrative and not restrictive. The scope of the invention is, therefore, indicated by the appended claims rather than by the foregoing description. All changes which come within the meaning and range of equivalency of the claims are to be embraced within their scope.

```
New
1     GOTO 60:REM        *I/O stepper (I=$(0), O=z(72))*
3     IF (xby(65507) .AND.64)=0 THEN Z(0)=XBY(65506) : GOTO 3
4     DO : WHILE (XBY(65507) .AND.128)=128
5     I=O : DO : I=I+1 : XBY(65506)=ASC($(0),I)
6     WHILE ASC(S( )),I)<>13 : RETURN
7     DO : WHILE (XBY(65507) .AND. 64)=64
8     I=0 : DO : Z(I)=XBY(65506)
9     I=I+1 : UNTIL Z(I-1)=32 : RETURN
10    REM *error check*
15    IF TX<0 THEN TX=0
16    RETURN
20    IF TX<-251 THEN TX=-251
21    RETURN
25    IF TX>251 THEN TX=251
26    RETURN
30    GOSUB 50:TP1=TP:T1=TIME
32    DO:UNTIL TME>T1+0.2
34    GOSUB 50 TP2=TP:T2=TIME
36    SL=(TP2-TP1)/(T-T1):IF SL<>0 THEN IT=(TG-TP2)/SL
```

-continued

| | |
|---|---|
| 38 | PRINT USING (###.##), "SL=", SL, "IT=", IT, "AT TEMP=", TP2 |
| 40 | IF IT>1 GOTO 30 |
| 42 | RETURN |
| 49 | REM *temperature measurement* |
| 50 | E=XBY(65504):F=XBY(65505):G=XBY(65504):TP=(F*256+G+300)/38.3: RETURN |
| 60 | CLEAR : STRING 150,72 : DIM Z(72) |
| 72 | DTEMP=95:DTIM=1:DS=10 |
| 74 | ATEMP=60:ATIM=1:AS=20 |
| 76 | ETEMP=74:ETIM=15:ES=1:CYCLE=100 |
| 80 | PRINT USING (###), "#", TAB (20), "TEMP", TAB (30), "TIME", TAB (40), "SLOPE" |
| 82 | PRINT "1) DENATURATION", TAB(20), DTEMP, TAB(30), DTIM, TAB (40), DS |
| 84 | PRINT "2) ANNEALING", TAB(20), ATEMP, TAB(30), ATIM, TAB (40), AS |
| 86 | PRINT "3) EXTENSION", TAB(20), ETEMP, TAB(30), ETIM, TAB (40), ES |
| 88 | PRINT "4) CYCLES ", CYCLE: PRINT |
| 110 | INPUT "TYPE # TO CHANGE OR O IF OKAY (CHOICES ARE 0,1,2,3 OR 4)?", J |
| 114 | IF J=0 THEN GOTO 170 |
| 116 | ON J GOSUB ,120, 130, 150, 160 |
| 118 | PRINT:GOTO 80 |
| 120 | INPUT "ENTER DENATURATION Temp, Time, Slope:", DTEMP, DTIM, DS |
| 125 | IF DTEMP>98 GOTO 120 |
| 126 | RETURN |
| 130 | INPUT "ENTER ANNEALING Temp, Time, Slope:", ATEMP, ATIM, AS |
| 140 | IF AS<0 GOTO 130 |
| 142 | IF AS>21 GOTO 130 |
| 145 | RETURN |
| 150 | INPUT "ENTER EXTENSION Temp, Time, Slope:", ETEMP, ETIM, ES |
| 160 | INPUT "ENTER Number of Cycles:", CYCLE:RETURN |
| 170 | $(0)=msrl 500;spl 200;hfl 2;rt2 1;esr" ; GOSUB 3: GOSUB 7 |
| 175 | FOR I=0 TO 10 : PRINT CHR(Z(I)), : NEXT I : PRINT |
| 200 | $(0) = gol nd;hfl 2;wfo = .x..;s1":GCSUB 3:      rem open |
| 210 | PRINT "WAIT FOR COOLING" : XBY(65504)=3 |
| 220 | DO : GOSUB 50 : UNTIL TP<45 |
| 230 | PRINT "TEMP=", TP," LOAD SAMPLES THEN PRESS A KEY" |
| 240 | W=GET : IF W=0 GOTO 240 |
| 300 | TMC=0 : WS=0 : Clock 0 ; TIME =0 : DBY(71)=0 : CLOCK 1 |
| 305 | $(0)='hfl 1;spl 100;gol;wfo =x...;s1":GOSUB 3: |
| 310 | FOR V=1 TO CYCLE |
| 315 | PRINT "D", : TG=DTEMP:XBY(65509)=4:IF V=1 THEN TG =DTEMP+(DS/4) |
| 320 | WS=(DS*10+WS*9)/10:TX=INT(WS+0.5) : GOSUB 15 |
| 325 | XBY(65508)=TX:GOSUB 50:IF TP>TG GOTO 340 |
| 330 | IF TX<>DS*10 GOTO 320 |
| 333 | GOSUB 30 |
| 335 | GOSUB 50:IF TP<TG GOTO 335 |
| 340 | TG=DTEMP:EB=TIME |
| 345 | WS=(5*WS+10*(TG-TP))/7:TX=INT(WS+0.5) |
| 350 | IF TX>=0 THEN GOSUB 25:XBY(65508)=TX:XBY(65509)=4 |
| 355 | IF TX<0 THEN GOSUB 20:XBY(65508)=0:XBY(65509)=4-TX |
| 360 | IF V=1 THEN IF DTIM+5>(TIME-EB) GOTO 380 |
| 370 | IF DTIM<(TIME-EB) GOTO 500 |
| 380 | GOSUB 50 : GOTO 345 |
| 500 | PRINT "A", :XBY(65508)=0: TG=ATEMP |
| 845 | $(0) = "spl 200;gol nd;hfl 2;wfo =.x.;s1":GOSUB 3:      rem open |
| 855 | XBY(65509)=AS*10 |
| 860 | GOSUB 30 |
| 890 | ES=TIME:WS=-AS*10 |
| 913 | WS=(4*WS+20(TG-TP))/5:TX=INT(WS+0.5) |
| 915 | IF TX>=0 THEN GOSUB 25:XBY(65508)=TX:XBY(65509)=4 |
| 918 | IF TX<0 THEN GOSUB 20:XBY(65508)=0:XBY(65509)=4-TX |
| 920 | IF ATIM+<(TIME-EB) GOTO 925 |
| 924 | GOSUB 50 : GOTO 913 |
| 925 | PRINT:PRINT "E ",:XBY(65509)=4:TG=ETEMP+1 |
| 930 | $(0)="hlf 1;spl 50;gol;wfo =x..;s1" GOSUB 3: WS=0: REM CLOSE |
| 935 | WS=(ES*10+WS*9)/10:TX=INT(WS+0.5):GOSUB 15:GOSUB 25:XBY(65508)=TX |
| 937 | GOSUB 50:IF TP>TG-1 GOTO 970 |
| 940 | IF TX<>ES*10 GOTO 935 |
| 950 | GOSUB50 : IF TP<TG-1 GOTO 950 |
| 970 | EB=TIME |
| 980 | WS=(WS+5*(TG-TP))/2 :TX=INT(WS+0.5) |
| 983 | IF TX>=0 THEN GOSUB 25:XBY (65508)=TX:XBY(65509)=4 |
| 987 | IF TX<0 THEN GOSUB 20:XBY(65508)=0:XBY(65509)=4-TX |
| 990 | IF ETIM<(TIME-EB) GOTO 1000 |
| 995 | GOSUB 50 : GOTO 980 |
| 1000 | CTIM=TIM-TMC : TMC=TIME : PRINT "CYCLE=", V, "TIME=", CTIM |
| 1050 | NEXT V |
| 1055 | XBY (65508)=0:XBY(65509)=255 |
| 1060 | INPUT "STRAND REANNEALING (Y/N) ?", $(1) |
| 1070 | IF ASC($(1),1)=78 GOTO 1390 |
| 1100 | PRINT "STRAND REANNEALING IN PROCESS..." |
| 1110 | TG=DTEMP:XBY(65509)=4 |

-continued

```
1120  WS=(DS*10+NS*9)/10:TX=INT(WS+0.5):GOSUB 15
1130  XBY (65508)=TX:GOSUB 50: IF TP>TG GOTO 1170
1140  IF TX<>DS*10 GOTO 1120
1150  GOSUB 30
1160  GOSUB 50:IF TP<TG GOTO 1160
1170  EB=TIME
1180  WS=(11*WS+10*(TG-TP))/12:TX=INT(WS+0.5)
1185  IF TX>=0 THEN GOSUB 25:XBY(65508) =TX:XBY(65509)=4
1190  IF TX<0 THEN GOSUB 20:XBY(65508)=0:XBY(65509)=4-TX
1193  IF 5<(TIME-EB) GOTO 1200
1196  GOSUB 50 : GOTO 1180
1200  XBY(65508)=0:XBY(65509)=255:WS=0
1210  DO:GOSUB 50: UNTIL TP<75
1220  EB=TIME
1230  WS=(WS+5*(75-TP))/3 :TX=INT(WS+0.5)
1240  IF TX>=0 THEN GOSUB 25: XBY(65508)=TX:XBY(65509)=4
1250  IF TX<0 THEN GOSUB 20:EXBY(65508)=0:XBY(65509)=4-TX
1260  IF 60<(TIME-EB) GOTO 1280
1270  GOSUB 50 : GOTO 1230
1280  XBY(65508)=0:XBY(65509)=255
1290  INPUT "ANOTHER RUN (Y/N) ?", $(1)
1300  IF ASC($(1),1)=78 GOTO 2000
1400  PRINT:$(0)="go1 nd;hfl 9;wfo =x..;s1"; GOSUB 3;GOTO 80
2000  $(0)="go1 nd;hfl 9;wfo = .x..;s1":GOSUB 3: END
```

What is claimed and desired to be secured by United States Letters Patent is:

1. A thermal cycler for amplifying a nucleic acid comprising:
    a housing comprising a chamber;
    a port in said housing for receiving at least one polymerase chain reaction (PCR) sample holder in said chamber;
    a heating assembly for heating a sample comprising a nucleic acid contained in said sample holder, wherein said heating assembly is in thermal communication with said PCR sample holder when said sample holder is present in said chamber;
    a cooling assembly for cooling said sample, wherein said cooling assembly is in thermal communication with said PCR sample holder when said PCR sample holder is present in said chamber; and
    a controller programmed to control said heating and said cooling assemblies to cycle said sample holder and said sample through a predetermined temperature cycle corresponding to the denaturation, annealing and elongation steps of a polymerase chain reaction within a time range of 30-60 seconds;
    wherein said PCR sample holder has a thermal mass which provides for completing said cycle of said polymerase chain reaction within said time range.

2. The thermal cycler of claim 1 wherein said heating assembly comprises a resistance heater.

3. The thermal cycler of claim 2 wherein said resistance heater comprises a heating coil.

4. The thermal cycler of claim 1 wherein said heating assembly is in fluid communication with said PCR sample holder when said PCR sample holder is present in said chamber.

5. The thermal cycler of claim 4 wherein said heating assembly comprises a blower.

6. The thermal cycler of claim 1 wherein said cooling assembly is in fluid communication with said PCR sample holder when said PCR sample holder is present in said chamber.

7. The thermal cycler of claim 6 wherein said cooling assembly comprises a blower.

8. The thermal cycler of claim 6 wherein said chamber comprises a fluid inlet and a fluid outlet to provide for the entry of ambient air and exhaust of heated air to cool said PCR sample holder when said PCR sample holder is present in said chamber.

9. The thermal cycler of claim 1 wherein said controller is capable of lowering the temperature of said PCR sample holder at a rate of at least about 1.5 degrees Celsius per second.

10. The thermal cycler of claim 7 wherein the motor for said blower is external to said chamber.

11. The thermal cycler of claim 1 in combination with said PCR sample holder.

12. The thermal cycler of claim 11 wherein said controller cycles the sample through said temperature cycle within the time range of 30-60 seconds.

13. The thermal cycler of claim 1 where said sample holder is a thin wall capillary tube.

* * * * *